(12) United States Patent
Erickson et al.

(10) Patent No.: US 9,057,099 B2
(45) Date of Patent: Jun. 16, 2015

(54) ENHANCED ON-CHIP SERS BASED BIOMOLECULAR DETECTION USING ELECTROKINETICALLY ACTIVE MICROWELLS

(75) Inventors: David Erickson, Ithaca, NY (US); Yun Suk Huh, Daejeon (KR); Carl A. Batt, Groton, NY (US); Adam Joseph Lowe, Syracuse, NY (US)

(73) Assignee: Cornell University, Ithaca, NY (US)

( * ) Notice: Subject to any disclaimer, the term of this patent is extended or adjusted under 35 U.S.C. 154(b) by 639 days.

(21) Appl. No.: 13/124,296

(22) PCT Filed: Oct. 14, 2009

(86) PCT No.: PCT/US2009/060675
§ 371 (c)(1),
(2), (4) Date: Aug. 18, 2011

(87) PCT Pub. No.: WO2010/045357
PCT Pub. Date: Apr. 22, 2010

(65) Prior Publication Data
US 2011/0294691 A1    Dec. 1, 2011

Related U.S. Application Data

(60) Provisional application No. 61/105,656, filed on Oct. 15, 2008.

(51) Int. Cl.
| | | |
|---|---|---|
| *C12Q 1/68* | (2006.01) | |
| *C12P 19/34* | (2006.01) | |
| *C07H 21/00* | (2006.01) | |
| *C07H 21/02* | (2006.01) | |
| *C07H 21/04* | (2006.01) | |
| *B01F 13/00* | (2006.01) | |
| *B01L 3/00* | (2006.01) | |
| *G01N 21/65* | (2006.01) | |

(52) U.S. Cl.
CPC .......... *C12Q 1/6827* (2013.01); *B01F 13/0076* (2013.01); *B01L 3/50273* (2013.01); *B01L 3/502761* (2013.01); *B01L 2300/0636* (2013.01); *B01L 2300/0654* (2013.01); *B01L 2300/0809* (2013.01); *B01L 2300/0829* (2013.01); *B01L 2300/0887* (2013.01); *B01L 2400/0415* (2013.01); *B01L 2400/0424* (2013.01); *C12Q 1/6862* (2013.01); *C12Q 2565/632* (2013.01); *G01N 21/658* (2013.01)

(58) Field of Classification Search
CPC .......... C12Q 1/68; C12P 19/34; C07H 21/00; C07H 21/02; C07H 21/04
USPC ................ 435/6.1, 91.2; 536/22.1, 23.1, 24.3
See application file for complete search history.

(56) References Cited

U.S. PATENT DOCUMENTS

| 4,988,617 | A  | * | 1/1991 | Landegren et al. .......... 435/6.11 |
|---|---|---|---|---|
| 5,266,498 | A  |   | 11/1993 | Tarcha et al. |
| 5,721,102 | A  | * | 2/1998 | Vo-Dinh ....................... 435/6.12 |
| 6,743,581 | B1 | * | 6/2004 | Vo-Dinh .......................... 506/39 |
| 2003/0211488 | A1 | * | 11/2003 | Mirkin et al. ..................... 435/6 |
| 2006/0019278 | A1 | * | 1/2006 | Lo et al. ........................... 435/6 |
| 2006/0147941 | A1 |   | 7/2006 | Su |
| 2006/0246460 | A1 | * | 11/2006 | Graham et al. ................... 435/6 |
| 2007/0128615 | A1 | * | 6/2007 | Su ..................................... 435/6 |
| 2009/0298197 | A1 | * | 12/2009 | Natan et al. ................... 436/501 |
| 2010/0291599 | A1 | * | 11/2010 | Tague et al. ................. 435/7.92 |

FOREIGN PATENT DOCUMENTS

| WO | WO-2006066180 A1 | 6/2006 |
|---|---|---|
| WO | WO-2007059514 A2 | 5/2007 |

OTHER PUBLICATIONS

Barany, F., Genetic Disease Detection and DNA Amplification Using Cloned Thermostable Ligase. PNAS 88:189 (1991).*
Ni et al., Immunoassay Readout Method Using Extrinsic Raman Labels Adsorbed on Immunogold Colloids. Analytical Chemistry 71:4903 (1999).*
Sobrino et al., SNPs in forensic genetics: a review on SNP typing methodologies. Forensic Science International 154:181 (2005).*
Wiedmann et al., Ligase Chain Reaction (LCR)—Overview and Applications. PCR Methods and Applications 3:551 (1994).*
Cao et al., Nanoparticles with Raman Spectroscopic Fingerprints for DNA and RNA Detection. Science 297: 1536 (Aug. 30, 2002).*
Chen et al., A Homogeneous, Ligase-Mediated DNA Diagnostic Test. Genome Research 8:549 (1998).*
Notification Concerning Transmittal of IPRP and International Preliminary Report on Patentability for International Application No. PCT/US09/60675 mailed Apr. 28, 2011 (6 pages).

(Continued)

*Primary Examiner* — Ethan C Whisenant
(74) *Attorney, Agent, or Firm* — Harris Beach PLLC

(57) ABSTRACT

A method for detecting target nucleic acids such as SNPs is provided. The method comprises performing a ligase detection reaction (LDR), performing surface enhanced Raman scattering (SERS) on the LDR, and analyzing the outcome of the LDR using analysis and/or quantification of the SERS by detecting an emitted Raman signature. The LDR-SERS method can be used for sensitive and specific detection of any nucleic acid sequence of interest. A microfluidic SERS detection device is also provided. The device comprises electrokinetically active microwells for mixing and concentrating analytes and in which analytes can be quantified. The device can be used for performing the LDR-SERS method in optofluidic chip format.

10 Claims, 19 Drawing Sheets

(56) References Cited

OTHER PUBLICATIONS

Figure 1:
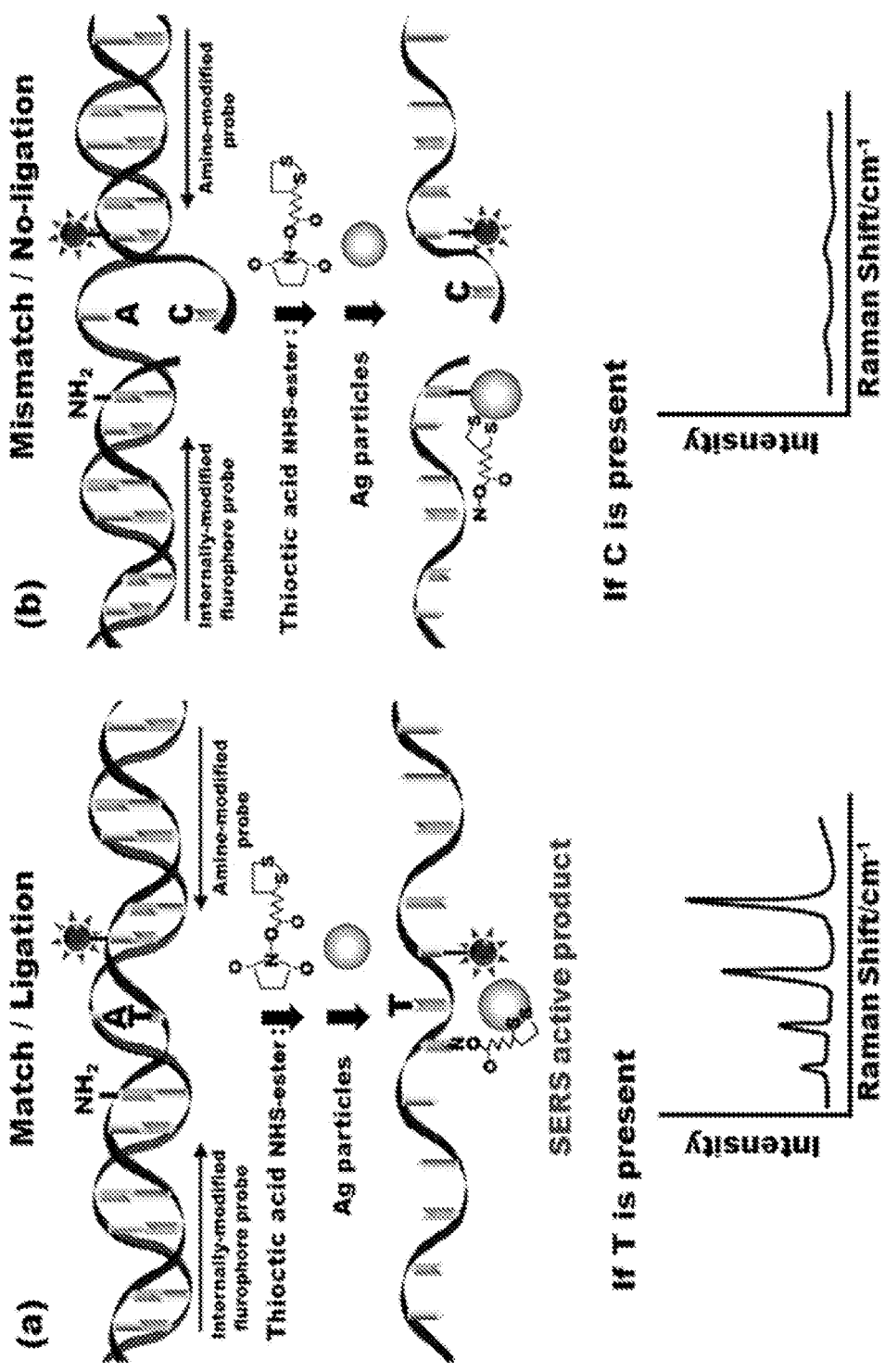

Extended European Search Report for corresponding EP Patent Application No. 09821197.2 dated Nov. 28, 2012 (9 pages).
Huh, Yun Suk et al., "Surface-Enhanced Raman Scattering Based Ligase Detection Reaction," J. Am. Chem. Soc., Feb. 18, 2009, vol. 131, No. 6 (pp. 2208-2213).
Lowe, Adam J. et al., "Multiplex Single Nucleotide Polymorphism Genotyping Utilizing Ligase Detection Reaction Coupled Surface Enhanced Raman Spectroscopy," Jul. 1, 2010, Anal. Chem., vol. 82, No. 13 (pp. 5810-5814).
Korean Intellectual Property Office, International Search Report for corresponding PCT Application No. PCT/US2009/060675, mailed May 4, 2010, (3 pgs.).
European Patent Office Office Action in corresponding EP Application No. 09821197.2 dated Jan. 24, 2014 (8 pages).
Dougan, Jennifer A. et al., "Enhanced oligonucleotide-nanoparticle conjugate stability using thioctic acid modified oligonucleotides," 2007 Nucleic Acids Research, vol. 35, No. 11 (pp. 3668-3675).
Su, Xing et al., "Composite Organic-Inorganic Nanoparticles (COINs) with Chemically Encoded Optical Signatures," 2005 Nano Letters, vol. 5, No. 1, pp. 49-54.

* cited by examiner

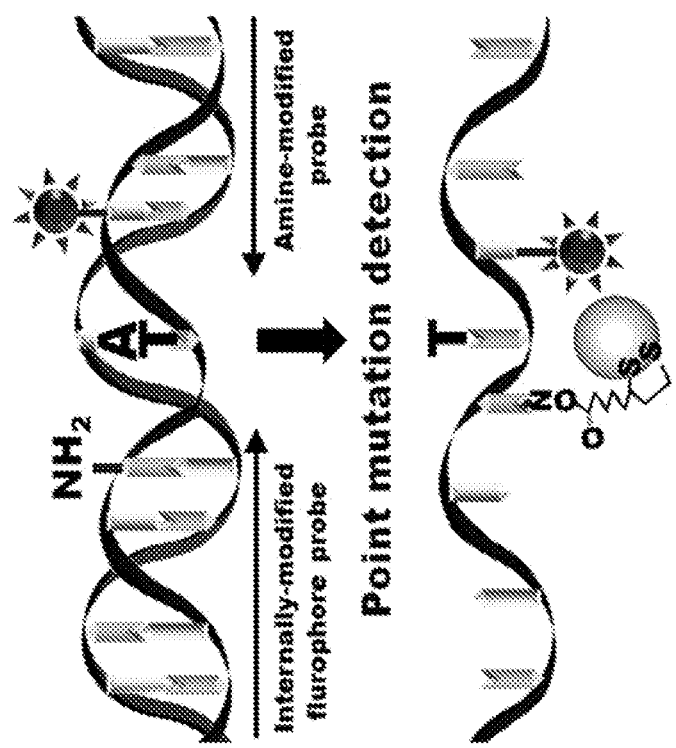
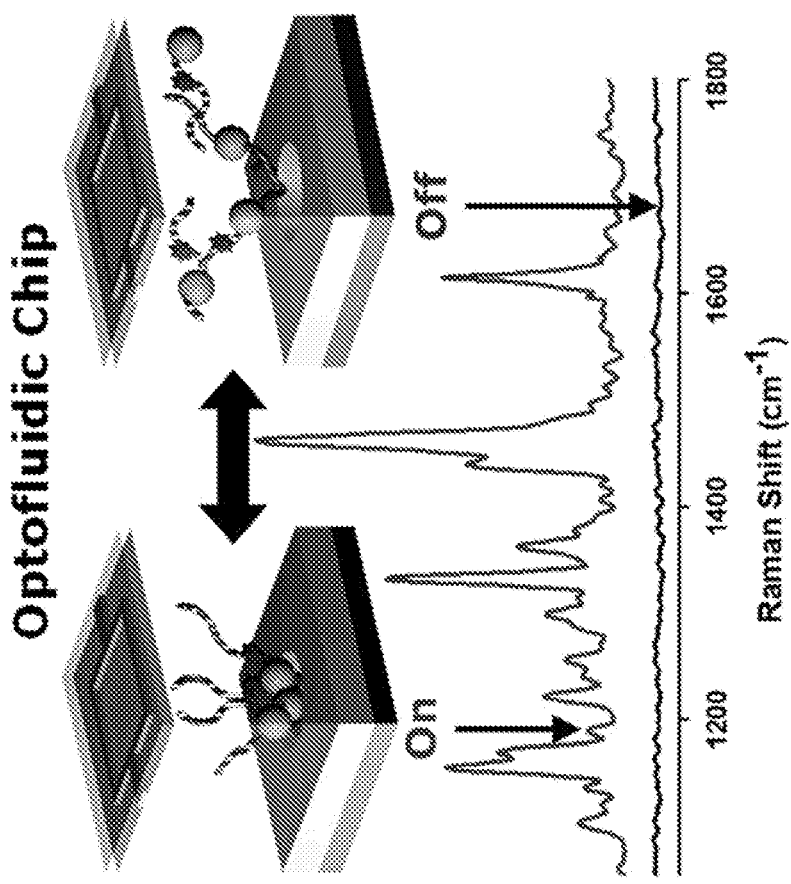
FIG. 6

ENHANCED ON-CHIP SERS BASED BIOMOLECULAR DETECTION USING ELECTROKINETICALLY ACTIVE MICROWELLS

CROSS-REFERENCE TO RELATED APPLICATIONS

This application is a national stage application under 35 U.S.C. §371 of PCT Application No. PCT/US2009/060675, filed Oct. 14, 2009, which claims priority to and the benefit of U.S. provisional patent application Ser. No. 61/105,656, entitled Enhanced on-chip SERS based biomolecular detection using electrokinetically active microwells, filed Oct. 15, 2008, which is incorporated herein by reference in its entirety.

STATEMENT REGARDING FEDERALLY SPONSORED RESEARCH OR DEVELOPMENT

The disclosed invention was made with government support under grant number R21EB007031 from the National Institutes of Health—National Institute of Biomedical Imaging and Bioengineering. The government has rights in this invention.

1. TECHNICAL FIELD

The present invention relates to method for detecting single nucleotide polymorphisms (SNPs). The invention further relates to methods detecting the results of ligase detection reactions (LDRs) using surface enhanced Raman scattering (SERS). The invention also relates to LDR primer compositions. The invention also relates to microfluidic devices for concentrating and mixing analytes. The invention further relates to methods for concentrating analytes and mixing them to increase the number of reactions in a given amount of time.

2. BACKGROUND OF THE INVENTION

2.1 Surface-Enhanced Raman Spectroscopy (SERS)

Surface-enhanced Raman spectroscopy (SERS) is a powerful vibrational spectroscopy technique. This output is molecularly specific and as such the spectrum obtained from SERS analysis provides much more detailed information about the molecular structure of the target molecule than those obtained using other spectroscopic techniques. There are two general approaches in which a SERS detection reaction can be carried out on chip: homogeneously, where target becomes bound or absorbs onto solution phase metallic nanoparticles that act as Raman enhancers, or heterogeneously, where solution phase targets interact with surface phase SERS active clusters such as roughened electrodes or precipitated silver or gold nanoparticles (NPs). The former approach has the same advantages as all homogeneous reactions (i.e. faster reaction rate and relative ease of implementation) as well as enhanced uniformity and repeatability of the SERS enhancement since the nanoparticles can be synthesized with high uniformity.

Park et al. (Park. T., et al. *Lab Chip*, 2005, 5, 437) has described the use of alligator-teeth-shaped PDMS microchannels to promote mixing between the target analyte and the metallic colloids used as SERS enhancers. One disadvantage of the homogeneous approach however is that because Raman enhancers are dispersed in solution, detection sensitivity are relatively low (unless enhanced microscopy techniques such as confocal are used).

Heterogeneous reactions using SERS active substrates, such as metal-film-over-nanosphere and nanowells, are also known in the art. While these systems can have fundamentally greater sensitivity (essentially concentrating: the detection zone from 3D to 2D), the analysis time is typically longer (since the molecules must diffuse to the analysis site), the chip fabrication is more complicated (since nanoscopic features must be patterned) and in some cases it is difficult to obtain regular and repeatable SERS enhancement.

To overcome this drawback. "optofluidic" based on chip SERS devices have been developed. For example Measor et al. (Measor. P., et al., *Appl. Phys. Lett.*, 2007, 90, 211107) used liquid core optical wave guides to confine the electromagnetic energy lengthwise though a hollow microchannel, allowing, it to interact with a greater number of particles. Wang et al. (Wang. M., et al., *Lab Chip*, 2007, 7, 630) used a nanochannel trap to collect solution Raman particles at a junction between a micro- and nanochannel. In the first of approach, the light/particle interaction is increased but the scattered light is still dispersed and thus the signal capture efficiency may be low. The second approach allows for physical concentration of the Raman enhancers but requires transport through a nanochannel, potentially limiting throughput.

2.2 Detection of Single Nucleotide Polymorphisms (SNPs) Using SERS

Single nucleotide polymorphisms (SNPs) are single base pair differences in DNA amongst individuals where the less common variant occurs in at least 1%) of the total population (Wang, D. G.; et al. *Science* 1998, 280, 1077; Aouacheria, A. et al. *Oncogene* 2005, 24, 6133). The decoding of the human genome has revealed more than 3 million SNPs (roughly 1 every 100-300 bases) and opened up exciting new capabilities for associating individual SNPs, haplotypes and linkage disequilibrium with disease states and pharmacological responses (Aouacheria. A. et al. *Oncogene* 2005, 24, 6133; Sachidanandam, R.; et al. *Nature* 2001, 409, 928). Owing to large-scale SNP discovery, genetic variation in the human genome is now an emerging resource for the study of cancer-related genes (Strausberg, R. L. et al. *Nat. Rev. Genet.* 2003, 4, 409; Qiu, P.; et al. *BMC Cancer* 2004, 4, 4). SNP's represent the most common variations across a genome and they can be used to directly detect alleles responsible for a trait of interest. Aouacheria, A. et al. *Oncogene* 2005, 24, 6133; Nakitandwe, J. et al. *Plant Methods* 2007, 3, 2).

Since cancer is at least in part caused by the accumulation of inherited and/or somatic mutations, SNPs are also emerging as an invaluable tool for cancer association studies. (Imyanitov, E. N. et al. *Cancer Lett.* 2004, 204, 3; Soucek, P.; et al. *J. Breast Cancer Res. Treat.* 2007, 103, 219), in some eases single base pair mutations are the direct cause of the cancer (Sidransky, D. *Nat. Rev. Cancer* 2002, 2, 210) while in others they represent well defined molecular markers indicative of an increased risk of cancer. In either case, numerous SNPs have been shown to be good biomarkers for many classes of cancer and have further been shown to correlate with various clinicopathological features of different cancer subtypes. (Soucek, P.; et al. *J. Breast Cancer Res. Treat.* 2007, 103, 21.9 Zheng, S. L. *N. Engl. J. Med.* 2008, 358, 910; Yoshiya, G. et al. *J. Gastraenterol. Hepatol.* 2008, 23, 948).

For example, point mutations in the proto-oncogene K-ras have been identified that induce its oncogenic function at codons twelve, thirteen, and sixty-one. (Forrester, K. et al. *Nature* 1987, 327, 298). Mutations in the BRCA genes associated with breast cancer also serve as a model. The p53 tumor suppressor gene and its negative regulator MdM2 have also been associated with oncogenic activation after various point mutations. (Soussi, T. et al. *Cancer Cell* 2007, 12, 303; Bond, G. L. et al. *Cancer Res.* 2005, 65, 5481).

Successive SNP-SNP interactions that may increase risk or severity of cancers have also been described. (Onay, V. U et al. *BMC Cancer* 2006, 6, 114). Analysis from SNP arrays have also shown that determination of copy number from specific SNP populations is also a useful indicator for cancer progression. (Kloth, J. N et al. *BMC Genomics* 2007, 8, 53), Polymorphisms themselves have additionally been linked as statistically significant indicators of cancer progression. (Sun, T. et al. *Clin. Cancer Res.* 2006, 12, 7009). Recently, SNPs have been identified as key markers in pharmacogenomics, the study of inheritable drug metabolism and reactivity, directly related to cancer treatment. (Sauna, Z. E. et al. *Cancer Res.* 2007, 67, 9609).

Faster and cheaper technological methods are needed to discover new SNPs, for genotyping them in many individuals, and ultimately for clinical diagnostics. (Risch, N. et al. *Science* 1996, 273, 1516; Kwok, P. Y. *Annu. Rev. Genomics and Human Genetics* 2001, 2, 235). All allele-specific SNP discrimination techniques suitable for high throughput genetic analysis can be categorized as primer extension, oligonucleotide ligation, invasive cleavage or hybridization based. (Kwok, P. Y. *Annu. Rev. Genomics and Human Genetics* 2001, 2, 235). There are numerous variants on the primer extension technique, however all are based on the ability of DNA polymerase to incorporate specific deoxyribonucleotides that are complementary to the sequence of the template DNA. (Sobrino, B. et al. *Forensic Sci. Int.* 2005, 154, 181; Perkel, *J. Nat. Methods* 2008, 5, 447).

Real-Time PCR or RT-PCR (Mhlanga, M. M. et al. *Methods* 2001, 25, 463; Socher, E. et al. *Anal. Biochem.* 2008, 375, 318; Satterfield, B. C. et al. *Clinical Chem.* 2007, 53, 2042) is likely of the simplest of these various methods. The reaction is carried out in a homogenous format and requires no post-PCR processing. This reduces the time and labor required for analysis while minimizing the number of potential sources of error and contamination.

To increase the specificity of the RT-PCR format for more stringent SNP detection, oligonucleotide ligation based methods can be used, e.g., Ligase Detection Reaction (LDR). (Kristensen, V. N. et al. *Biotechniques* 2001, 30, 318; Khanna, M et al. *Oncogene* 1999, 18, 27; Favis, R.; Barany, F. *In Circulating Nucleic Acids in Plasma or Serum* 2000; Vol. 906, p 39-43). In LDR, two primers anneal onto the DNA template at the site of a SNP. A discriminating base complementary to the wild template (WT) or mutant (MT) allele is present at the 3' end of the upstream primer. A downstream primer common to both alleles is also present in the reaction. If the primers match the template perfectly, ligation occurs. Ligation will not occur if the primer and template are mismatched at the discriminating base. The ligation, which permanently links the two primers together, can be detected with a variety of different methods, including FRET (Fang, C. et al. *Biosen. Bioelectro,* 2008, 24, 216) and autoradiography (Prigent, C. et al. Mol. Cell Biol. 1994, 14, 310; Qian, X. et al. *Am. Chem. Soc.* 2008, 130, 14934).

Most existing LDR and RT-PCR protocols use fluorescence tags (McNamara, D. T et al. Am. *J. Trop. Med. Hyg.* 2006, 74, 413) as reporters and thus all have the same fundamental limitation in that spectral overlap between the reporter dyes limits the degree to which the reactions can be multiplexed. Typical florescent dyes have an emission spectrum with a full width-half maximum on the order of 50 nm. Thus over the useful detection range of the spectrum (about 500 nm to 750 nm), one can at maximum expect to be able to discriminate on the order of 6 different dyes. This extends then to single tube reactions in that a maximum of 5 different SNPs can be screened for at once (1 color is used as an internal calibration).

SERS based techniques for sequence specific DNA detection have also been developed. Cao (Cao, Y. C. et al. *Science* 2002, 297, 1536) demonstrated a three-component sandwich assay using Ag staining on Au seed particles to enhance SERF, signals in DNA microarray format. Fabris et al. (Fabris. L. et al. *J. Am. Chem. Soc.* 2007, 129, 6086) developed a peptide nucleic acid (PNA) based SERS DNA assay that enabled more rapid hybridization rates since the neutrally charged PNA were not limited by the typical electrostatic repulsion between complementary DNA strands.

A number of so called "molecular beacon" based SERS probe techniques have also been developed (Vo-Dinh, T. IEEE *J. Sel. Top Quant.* 2008, 14, 198; Wabuyele, M. B. et al, *Anal. Chem.* 2005, 77, 781.0; Jung, J. et al. *Anal. Bioanal. Chem.* 2007, 387, 2609). These methods typically use a DNA hairpin structure with a Raman active molecule at one end and a metallic nanoparticle at the other that become separated following a hybridization thereby reducing the strength of the emitted SERS signal. Qian et al. (Qian, X. et al. *Am. Chem. Soc.* 2008, 130, 14934) and Graham et al. (Graham, D. et al. *Nat. Nano* 2008, 3, 548) have also recently presented dye-coded DNA functionalized metal nanoparticles—based SERS methods that enabled greater sensitivity and repeatability in obtaining the SERS spectrum.

To increase the number of molecular markers that can be screened for in a single step, there is a need in the art for simple detection systems for nucleic acid sequences such as SNPs that overcome the spectral overlap limitations of existing systems and that can be used in multiplex format.

Citation or identification of any reference in Section 2, or in any other section of this application, shall not be considered an admission that such reference is available as prior art to the present invention.

3. SUMMARY OF THE INVENTION

A method for detecting a binding pair of interest is provided. The method can comprise the steps of:
performing a molecular binding reaction;
performing surface enhanced Raman scattering (SITS) on the hybridization reaction; and
analyzing the outcome of the hybridization reaction, wherein the analyzing step comprises detecting an emitted Raman signature.

In one embodiment, the method detects a nucleic acid sequence of interest.

In another embodiment, the molecular binding reaction is a nucleic acid hybridization reaction.

In another embodiment, the nucleic acid hybridization reaction is a ligase detection reaction (LDR) or a ligase chain reaction (LCR).

In another embodiment, the binding pair of interest comprises a nucleic acid sequence of interest.

In another embodiment, the nucleic acid sequence of interest is a SNP or point mutation.

In another embodiment, the method can comprise the steps of:
i) providing at least one pair of ligase detection reaction (LDR) primers:
ii) amplifying a sample of a nucleic acid sequence of interest;

iii) mixing the primers and the sample for a desired period of time;

iv) optionally concentrating the sample with or without bound primers;

v) probing the sample with a laser;

vi) detecting, a surface enhanced Raman scattering (SERS) signal;

vii) analyzing the SERS signal, wherein the analyzing step comprises detecting a LDR primer signal; and viii) identifying the nucleic acid sequence of interest associated with the detected LDR primer signal.

In another embodiment, the nucleic acid sequence of interest is a SNP, the method further comprises the step of:

quantifying an SNP allelic ratio;

wherein the ratio is quantified based on relative intensity of signal output.

In another embodiment, the method can be carried out in multiplex format.

In another embodiment, a plurality of signals from binding pairs is detected.

In another embodiment, the binding pair of interest comprises a plurality of binding, pairs, the method further comprising, the step of:

disambiguating multiple SERS signals.

In another embodiment, the plurality comprises 2-30 binding pairs. In another embodiment, 30 or more binding pairs are detected.

In another embodiment, multiple wavelengths are interrogated; and a plurality of emitted Raman signatures is detected.

In another embodiment, the LDR or LCR employs a first primer and a second primer, and a Raman enhancer is bound to the first primer and a Raman reporter is bound to the second primer.

In another embodiment, the Raman enhancer is an Au, Ag, Cu or Na, Li, Al, Pa, In, Zn or Cd nanobead.

A composition is also provided. The composition can comprise a first nucleic acid primer, the first primer comprising a Raman enhancer bound internally in the first primer.

In one embodiment, the composition can further comprise a second nucleic acid primer, the second primer comprising a Raman reporter hound to the second primer.

In another embodiment, the Raman reporter is bound internally.

In another embodiment, the Raman enhancer of the first primer and the Raman reporter of the second primer are hound at locations that bring them into proximity when bound to a nucleic acid sequence matching both the first and second primers, and the Raman signal from the Raman reporter can be detected upon ligation of the first and the second primers ire the presence of the nucleic acid sequence matching both the first and second primers.

In another embodiment, the locations are internal locations.

In another embodiment, the first primer is a LDR or LCR primer.

In another embodiment, the first and second primers are a pair of LDR or LCR primers.

In another embodiment, the binding of the Raman enhancer to the first primer is mediated by binding of the Raman enhancer to an exposed amine group on the first primer.

In another embodiment, the exposed amine group on the first primer is an amine-modified deoxythymidine with a c6 spacer.

A method for a producing a Raman enhancer for LDR or LCR is also provided. In one embodiment, the method comprises a. designing an amine-labeled primer such that a reactive amine is moved away from the ligation site;

b. introducing a hairpin into the primer;

c. reacting amine-labeled primer with NHS ester of thioctic in aqueous solution; and d. binding reacted product to nanoparticles prior to ligation, wherein the nanoparticles are Raman enhancer nanoparticles.

A microfluidic SERS detection device is also provided. The device can comprise:

a lower substrate, wherein the lower substrate comprises a lower electrode, the lower electrode being an attraction electrode;

a dielectric layer, wherein at least one microchannel and one microwell are positioned in the dielectric layer, and an upper electrode.

In one embodiment, the lower electrode is a Ti/Au electrode deposited on the lower substrate.

In another embodiment, the upper electrode is an electrically functionalized electrode. In another embodiment, the electrically functionalized electrode is a PDMS gold electrode, In another embodiment, the microfluidic SERS detection device can comprises a PCR thermal cycler, a chamber for mixing ligase detection reaction (LDR) primers and amplified sample, a laser, or a SERS detector.

In another embodiment, the microfluidic SERS detection comprises an electrokinetically active microwell.

In another embodiment, the microfluidic SERS detection device comprises a chamber, wherein the electrokinetically active microwell is positioned in the chamber, the lower electrode is positioned below the microwell and the upper electrode is positioned near or above the microwell and in the chamber.

In another embodiment, the microfluidic SERS detection device comprises an optical ring resonator.

A method for increasing the number of reactions among analytes in a given amount of time is also provided. In one embodiment, the method comprises the steps of:

providing a microfluidic SERS detection device that comprises an electrokinetically active microwell;

placing a sample of the analytes interest in the electrokinetically active microwell; and applying alternating electrical biases across electrodes in the electrokinetically active microwell to cause the analytes to be pulled into the microwell and expelled from the microwell.

In another embodiment, the analytes are binding partners for a molecular binding reaction.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Overview of SERS-enhanced PCR/LDR detection reaction.

Figure 2:
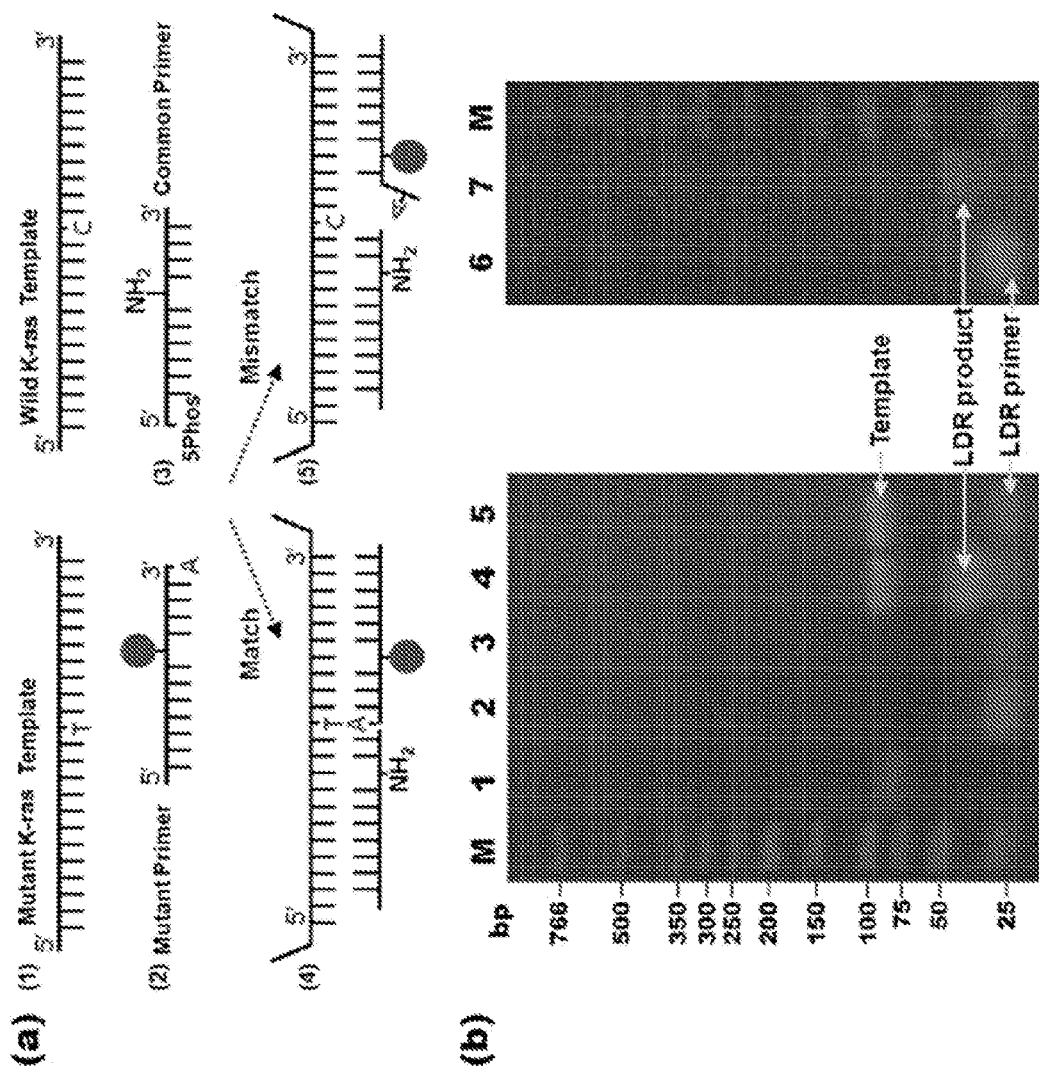

FIG. 2. Ethidium bromide-stained agarose gel showing the results of LDR-SERS reaction. (a) Schematic of reaction, (b) Standard marker (lane 1), templates (lane 2), mutant LDR primer (lane 3). LDR product by MT template (lane 4), LDR product by WT template (lane 5), final LDR-SERS products purified from lane 5 and lane 4, respectively (lane 6 and 7).

Figure 3:
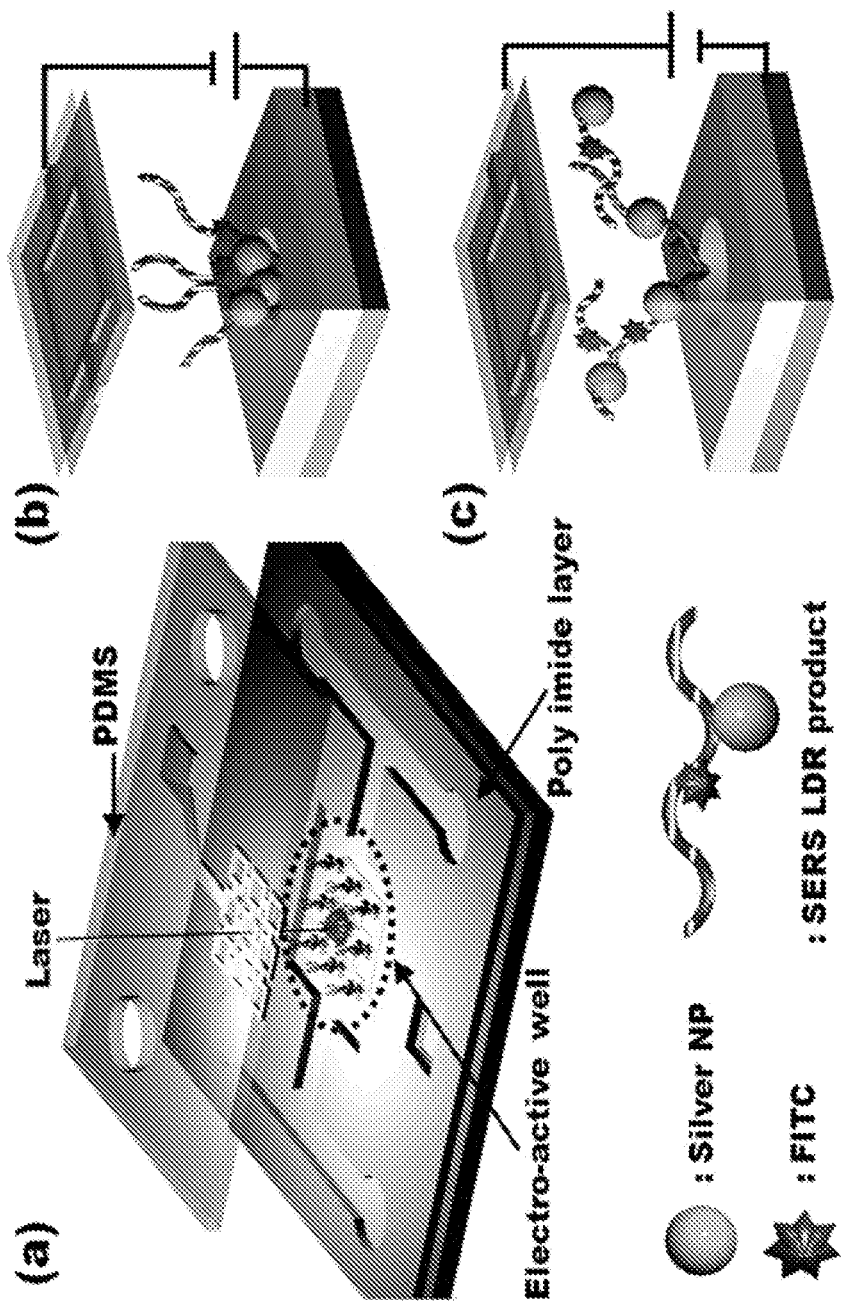

FIG. 3. (a) Electroactive microwell device for LDR-SERS based SNPs detection. Schematic representation of the system showing the lower electrode on the Pyrex glass substrate, the microwell array (diameters of 10 μm and height of 8 μm) and the upper electrically functionalized PDMS gold electrode. Applying the polarity shown in (b) attracts particles and (c) rejects them.

Figure 4:
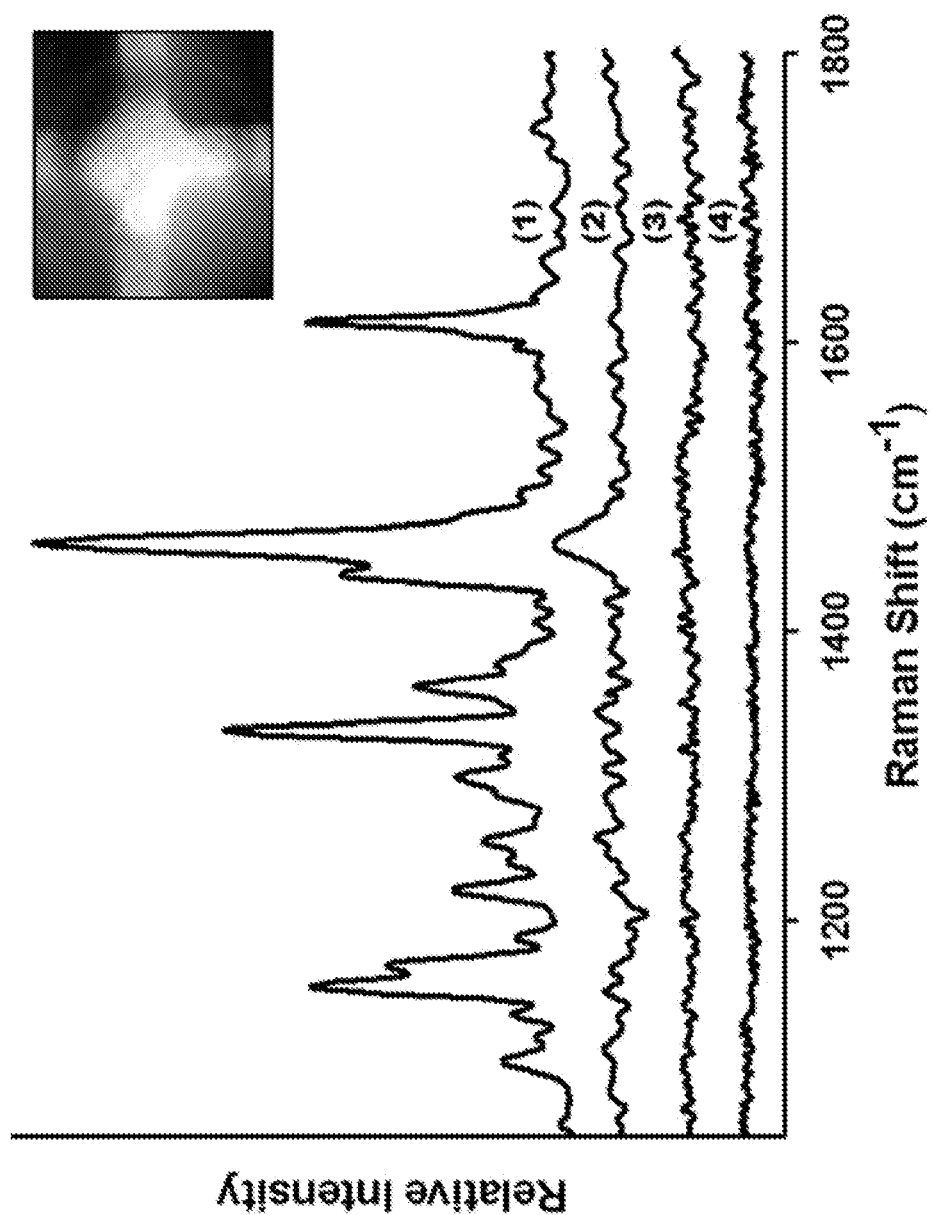

FIG. 4. SERS spectra collected on-chip for (1) positive sample containing FMdt-labeled LDR-SERS products by the mutant template, (2) negative sample reacted by wild type template, (3) control sample containing silver particles and DNA and (4) background control sample containing silver particles and linker. The concentration of each SNP is 100 pM. The inset shows the correct spectroscopic fingerprints corresponding to FMdT-labeled dye, suggesting positive detection.

Figure 5:
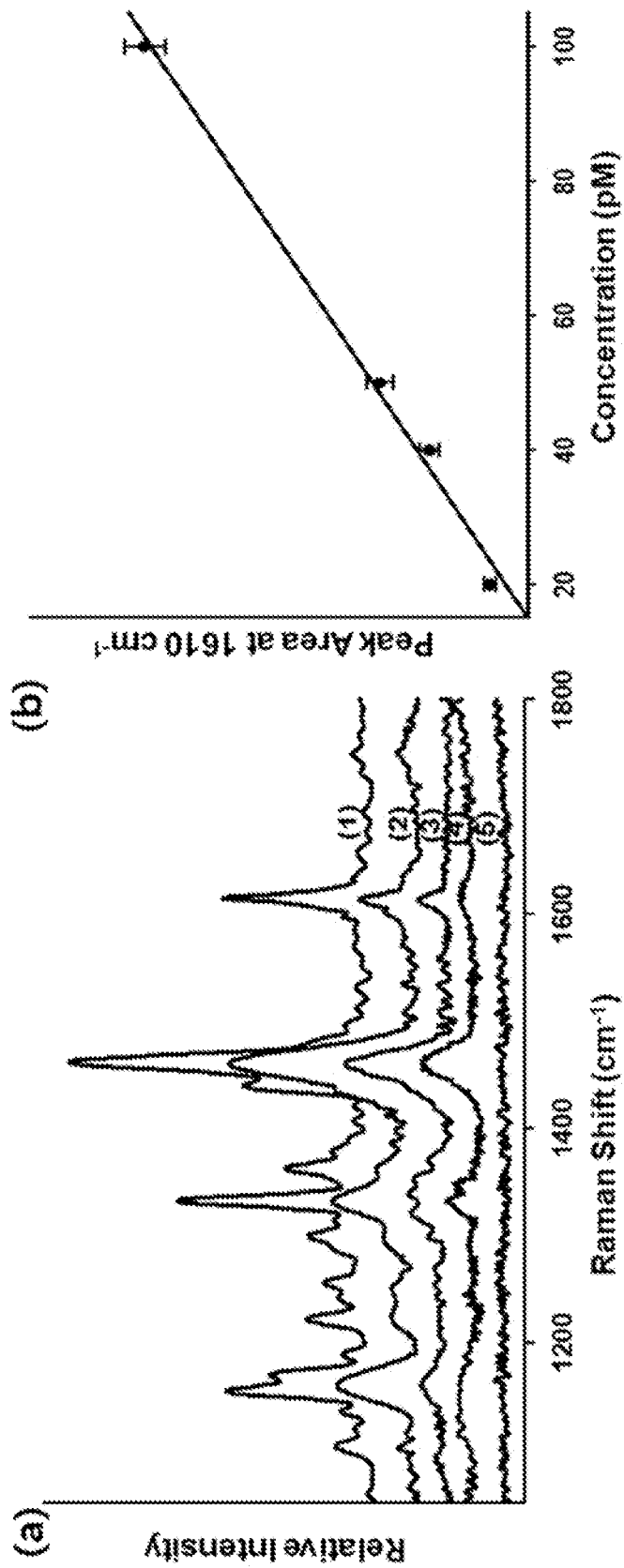

FIG. 5. (a) SERS spectra of FMdT-labeled MT in a microwell with the different concentrations of LDR-SERS products. (1) 100 pM, (2) 50 pM, and (3) 40 pM, (4) 20 pM, and (5) 10 pM LDR-SERS samples. (b) Plot of peak area at 1610 cm$^{-1}$ as a function of concentration (correlation coefficient: R-0.993). Note that the 10 pM result is omitted from (b) since the concentration was below the limit of detection.

FIG. 6. Overview of an exemplary embodiment of the LDR-SERS method for detecting target nucleic acid sequences. In this embodiment, the method is conducted in a microfluidic SERS detection device ("optofluidic chip") and used for detection of point mutations.

Figure 7:
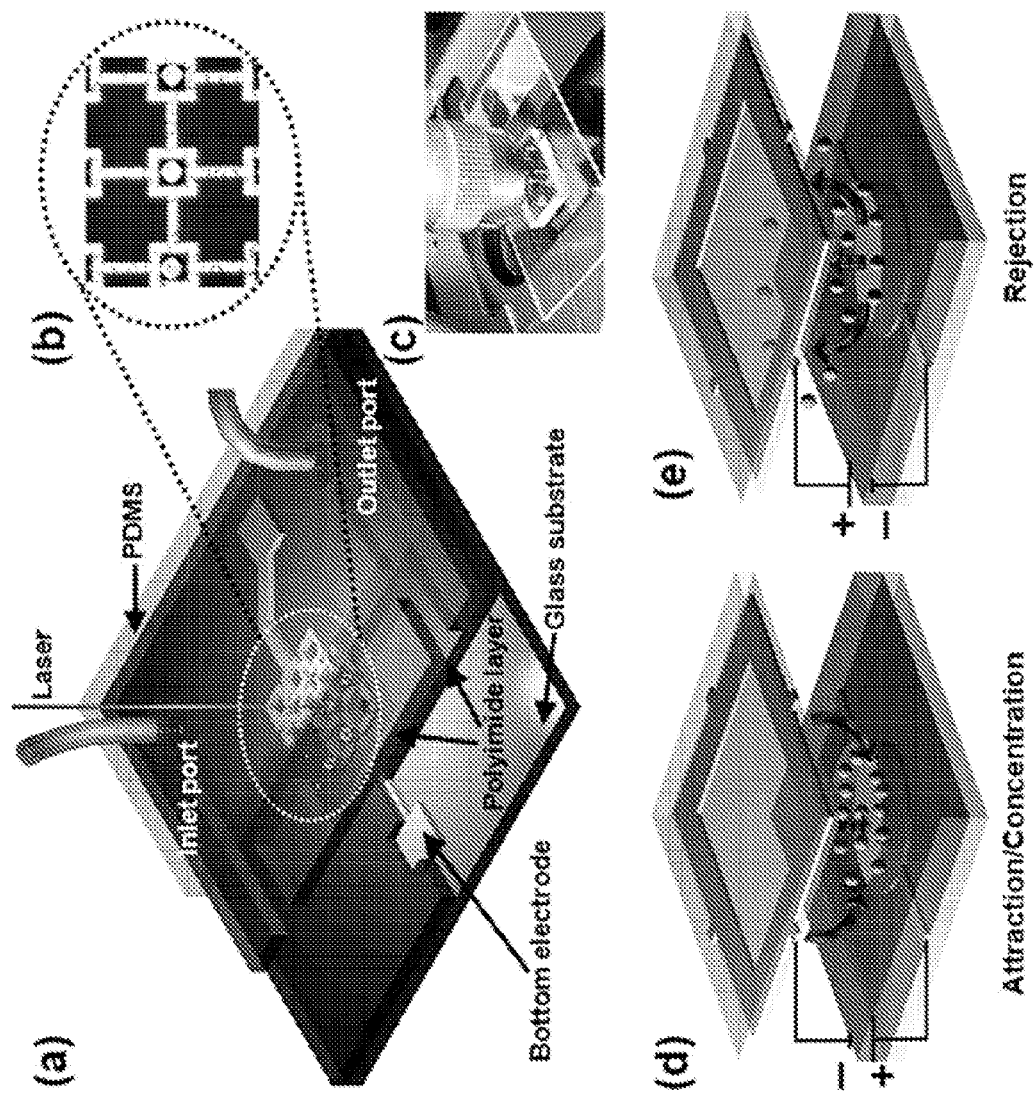

FIG. 7. Illustration of electroactive microwell device for SERS based nucleic acid detection (a) Schematic representation of the system showing the lower electrode on the Pyrex glass substrate, the microwell array (diameters of 10 μm and height of 8 μm), and the upper electrically functionalized PDMS gold electrode. Microchannels used to transport the sample and Raman enhancers into the mixing chamber are labeled as inlet ports. (b) The upper gold electrode patterned PDMS layer (c) The optical arrangement for recording the SERS signal. (d)-(e) 10 μm electroactive microwells are used to attract and concentrate SERS enhancers from the solution so they can be optically probed. Applying the polarity shown in (d) attracts particles and (e) rejects them.

Figure 8:
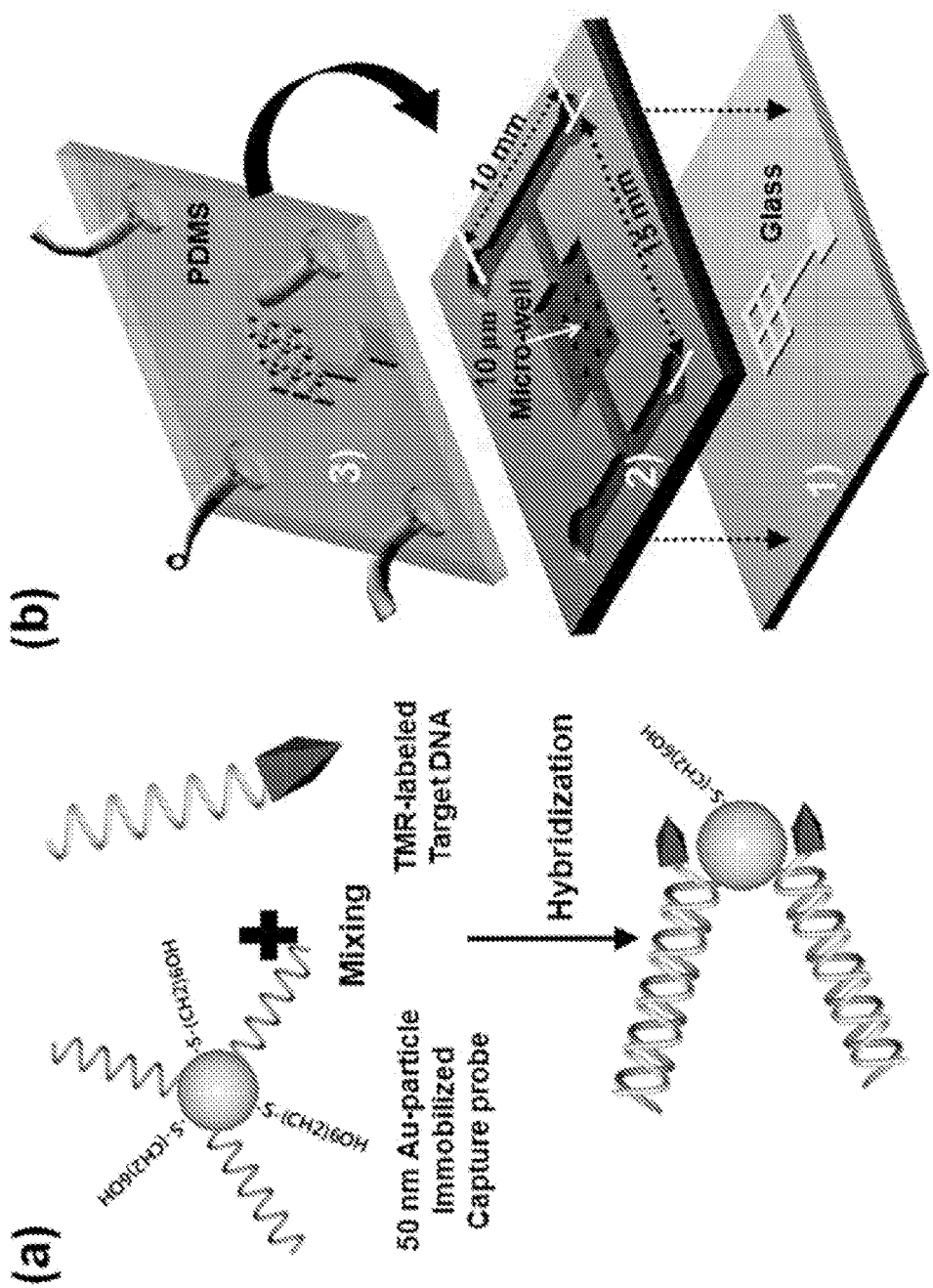

FIG. 8. (a) Schematic of the DENV-2 hybridization reaction, 50 nm gold NPs used as SERS enhancers, and technique for limiting non-specific adsorption. (b) Overview of chip fabrication process: 1) Ti/Au was deposited onto Pyrex glass substrate as a lower electrode. 2) Microwells with 10 μm size were fabricated with 8 μm thickness of polyimide dielectric layer. 3) An additional polyimide layer was inserted to form microfluidic channel. 4) Au was transferred onto the PDMS layer as an upper electrode. Final device dimensions are 10.0 (width)×15.0 (length)×0.16 (height) mm.

Figure 9:
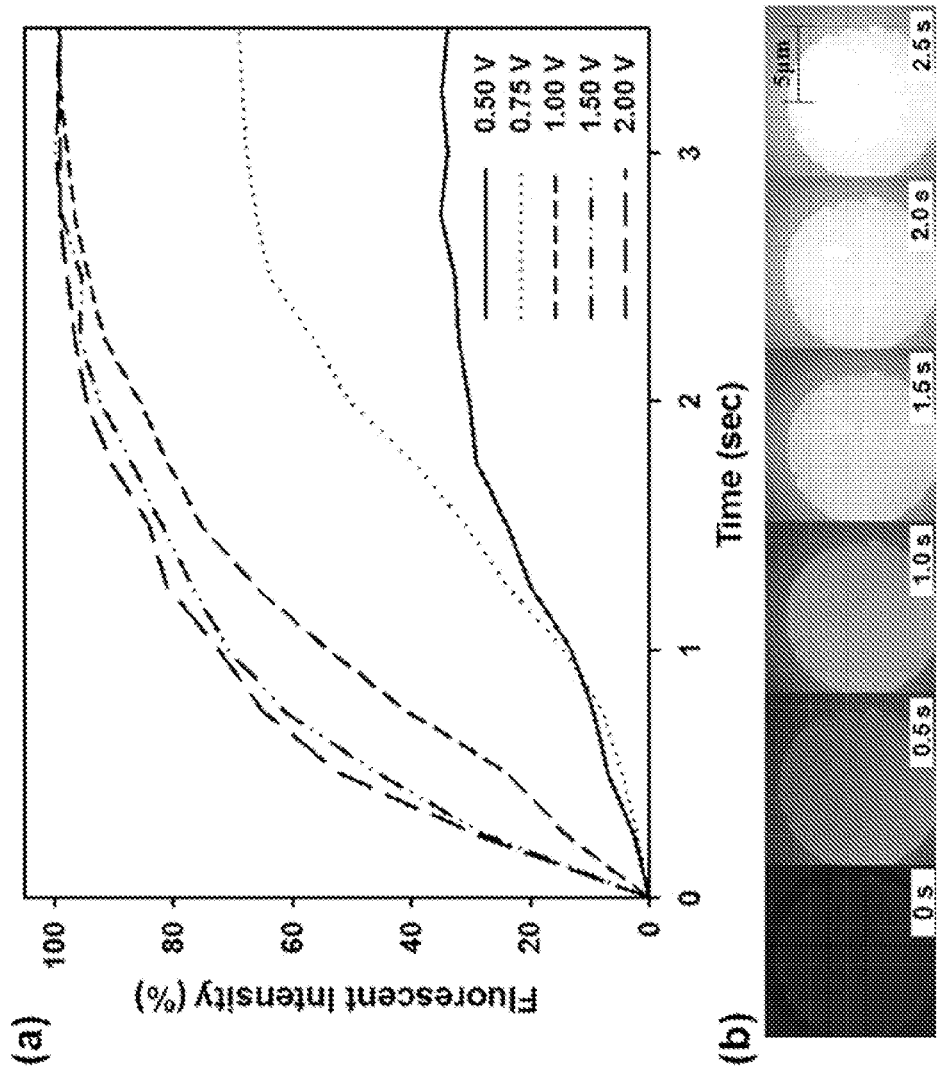

FIG. 9, (a) Efficiency of concentration for 44 nm PS particles into a 10 μm diameter with different applied potentials. (b) Time-lapse captured concentration images of 44 nm fluorescent PS particles from the bulk solution into the well for 2.5 s under a 1 V applied potential.

Figure 10:
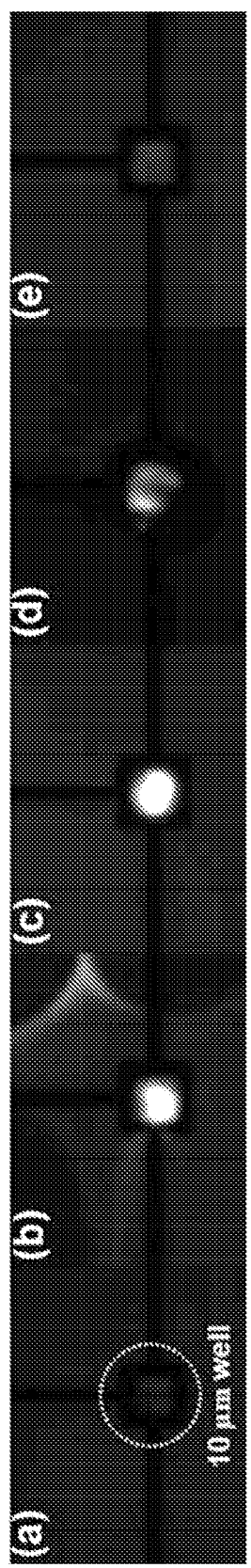

FIG. 10. Time-lapse images of concentration and ejection of 44 nm PS particles in a 10 μm well under 1.0 V potential. (a) Inactive microwell, (b) Particle attraction begins and beads are drawn into well, (c) Microwell after 5 s of attraction, (d) Particles are ejected from the well by reversing the polarity, (e) Microwell after 5 s rejection.

Figure 11:
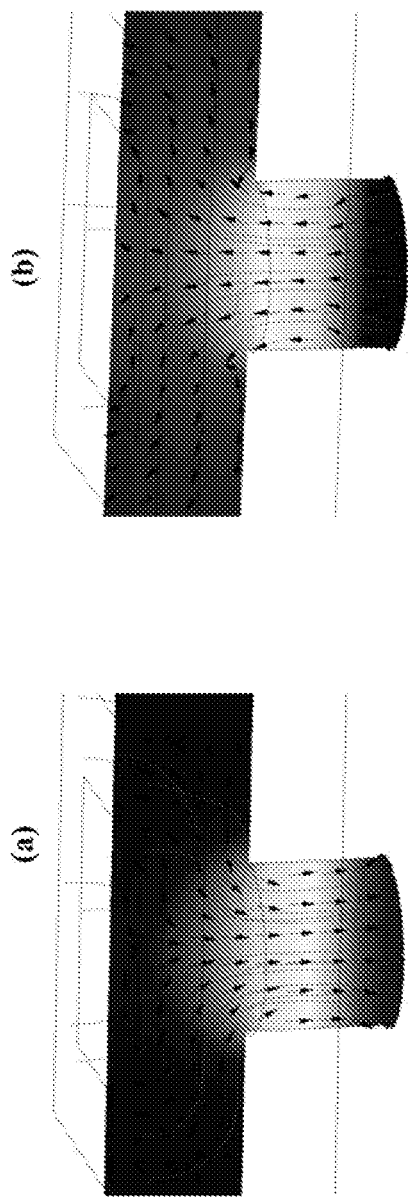

FIG. 11. Finite element simulations of the transport process of mixing. (a) Net electrokinetic transport streamlines for trapping, (b) Streamlines when potential polarity is reversed.

Figure 12:
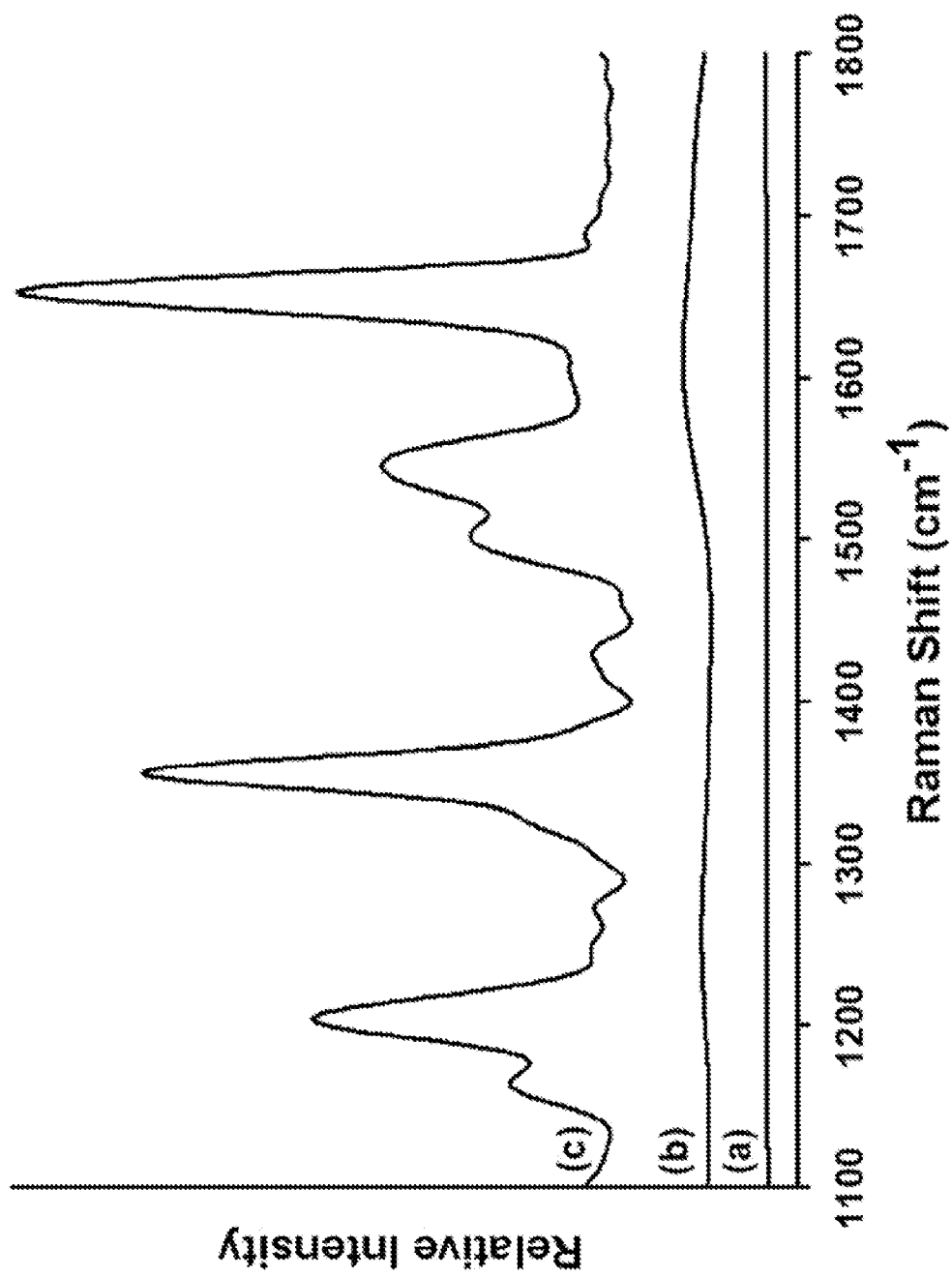

FIG. 12. (a) SERS spectra of gold NPs after immobilization of capture probes and application of MCH to protect against non-specific absorption. (b) SERS spectra after hybridization with DENV-4a (negative, control) and (c) with DENV-2a (target DNA) using the functionalized gold NPs. The concentration of each target DNA in hybridization reaction is 3 nM.

Figure 13:
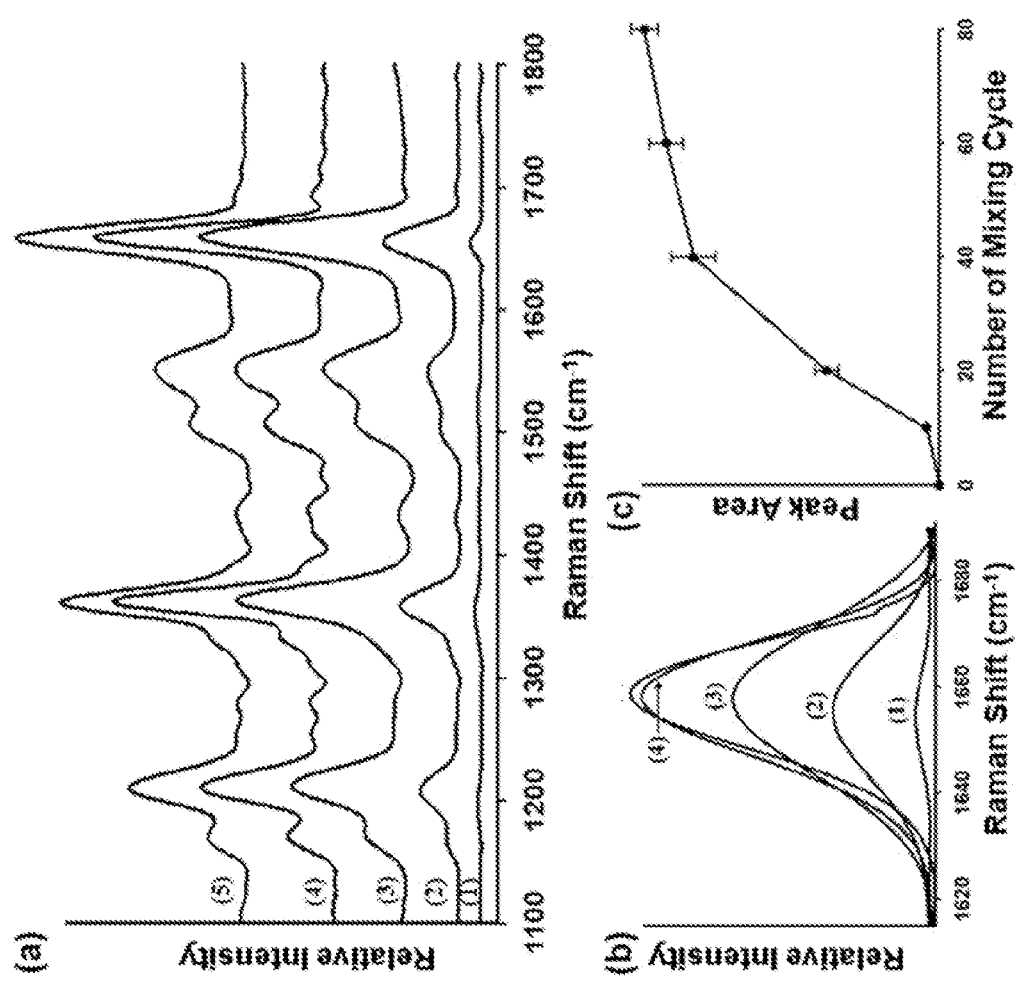

FIG. 13. (a) SERS spectra of TAMRA-labeled dengue virus serotype 2 with increasing the number of mixing cycles. (1) 10 cycles, (2) 20 cycles, (3) 40 cycles, (4) 60 cycles, and (5) 80 cycles. (b) SERS spectra from 1610 to 1700 cm$^{-1}$ corresponding to each case illustrated above. (c) The variation in Raman peak as a function of mixing cycle. The concentration of target DNA was 3 nM.

Figure 14:
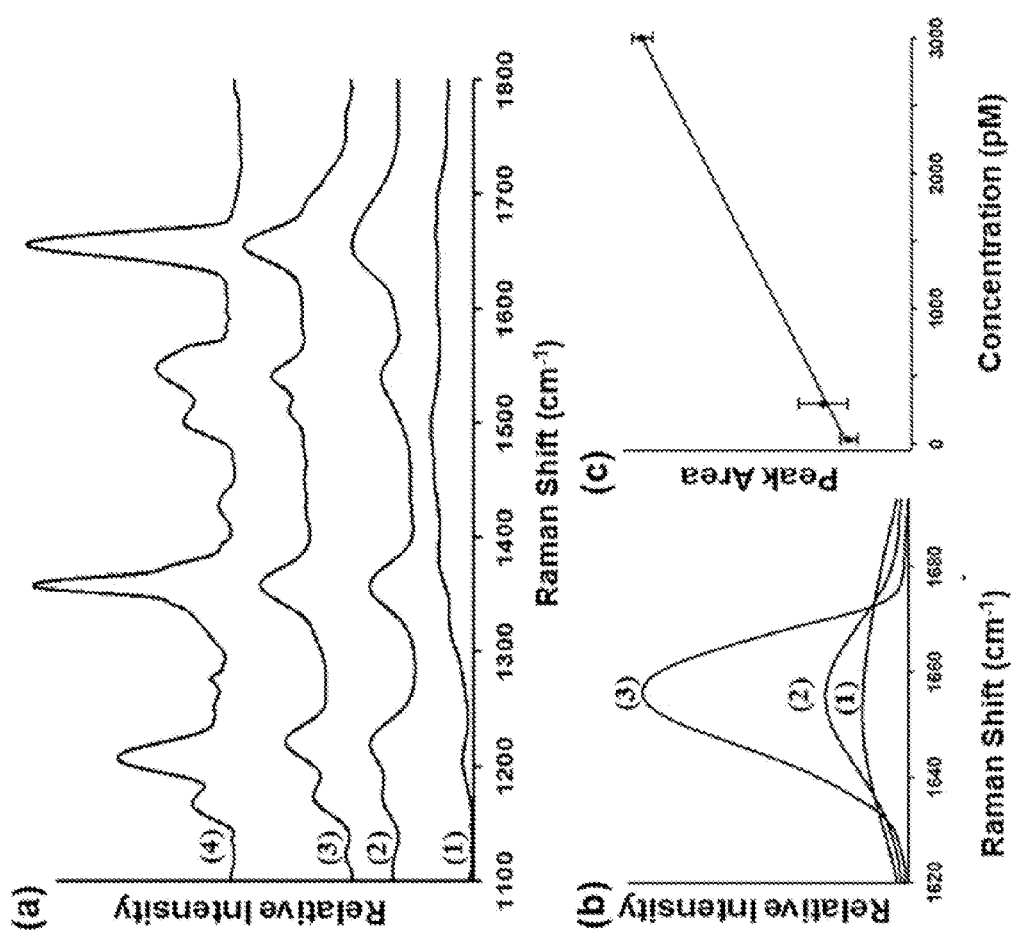

FIG. 14. (a) SERS spectra of TAMRA-labeled DENV-2 onto the gold NPs at different concentrations. Under applied potential, gold NPs was trapped to form SERS-active clusters with predictable position in 10 μm well. (1) 3 pM, (2) 30 pM, (3) 300 pM, and (4) 3000 pM. Raman peaks for the TAMRA-labeled DENV-2 were found at 1653, 15439, 1505, 1360, 1219, and 1170 cm$^{-1}$. (b) SERS spectra from 1610 to 1700 cm$^{-1}$ corresponding to each case illustrated above. (c) Plot of normalized peak area as a function of concentration.

Figure 15:
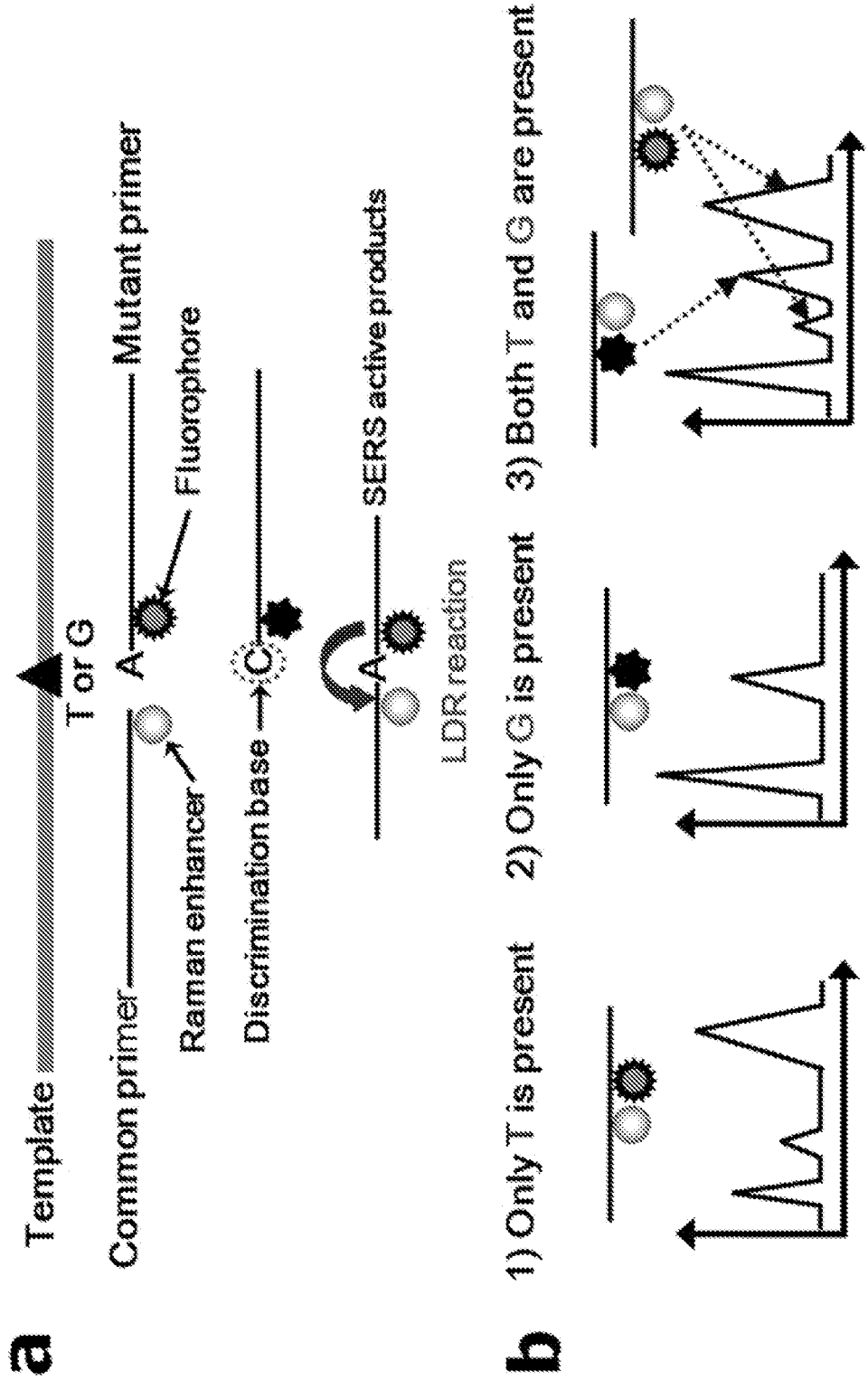

FIG. 15. a) Overview of LDR/SERS ligation. b) Schematic of multiplex SERS spectra.

Figure 16:
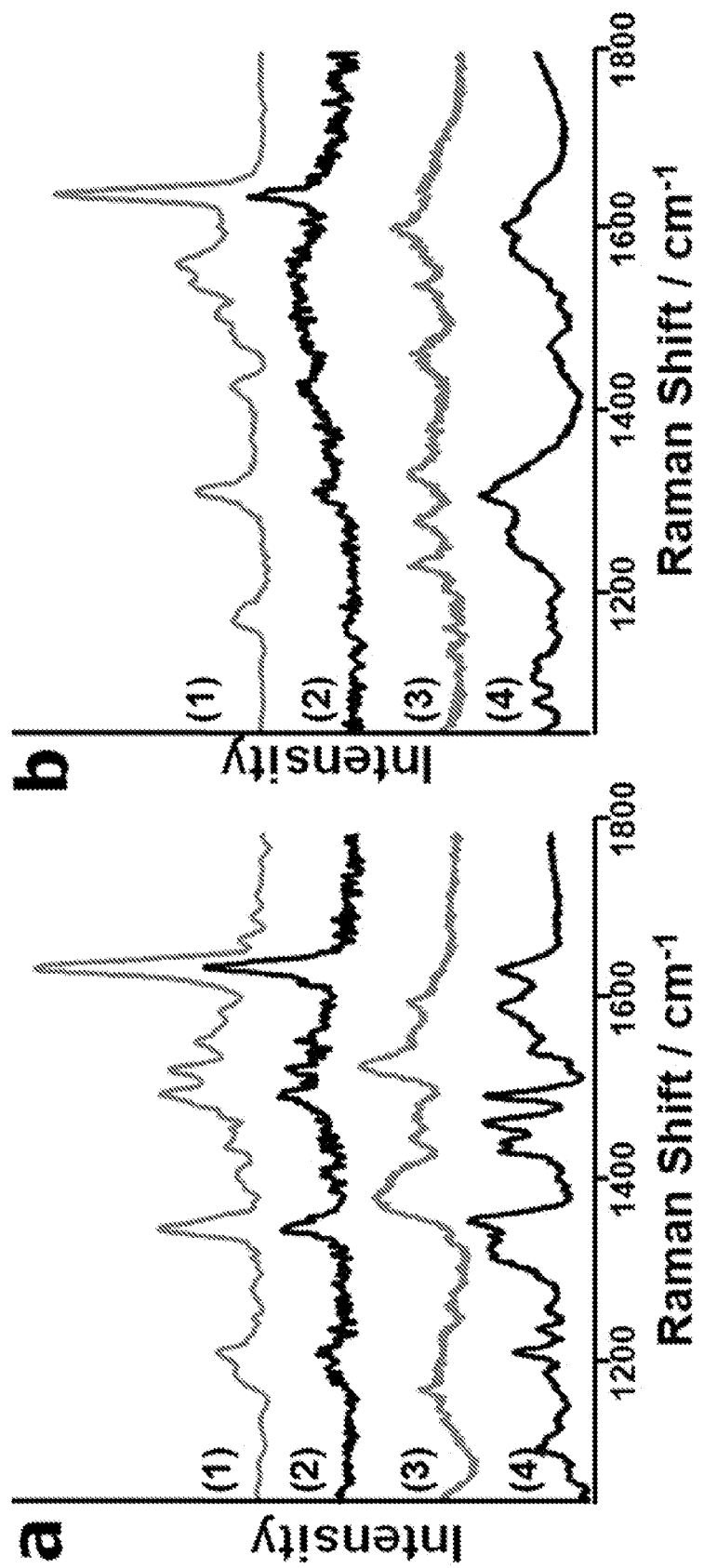

FIG. 16. Investigation of Raman enhancers and excitation source. Samples 1 and 2 were excited at 488 nm while samples 3 and 4 were excited at 785 nm. Odd numbered samples contained silver Raman enhancers and even numbered samples contained gold Raman enhancers, a) Wild Type TAMRA labeled DNA. b) G12D mutant fluorescein labeled DNA.

Figure 17:
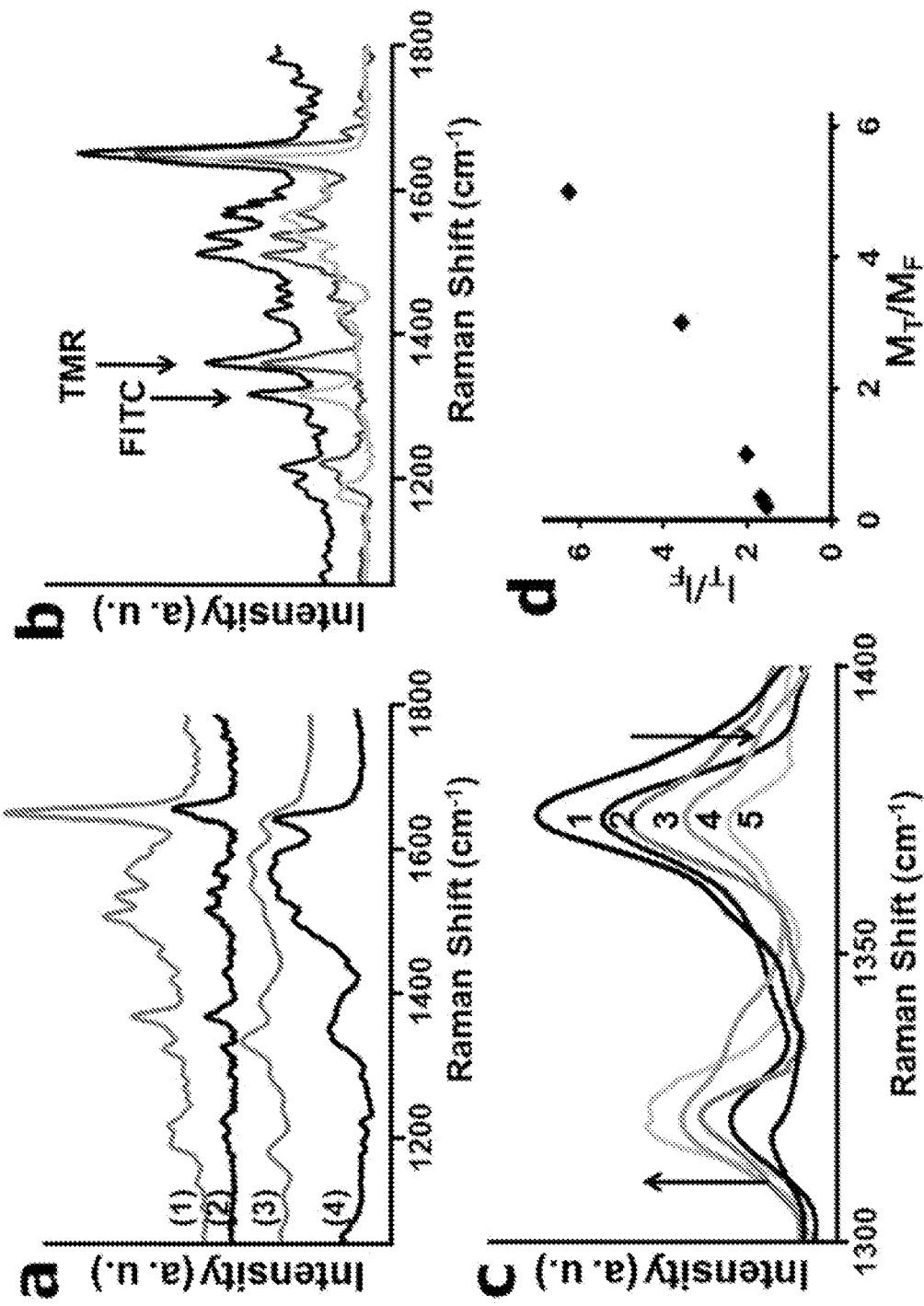

FIG. 17. Two-plex SNP Samples, a) Mixed genotype SERS spectra. b) Overlay of singleplex SERS spectra with WT in dark grey and mutant in light grey against the multiplex spectrum in black. TAMRA and fluorescein diagnostic peaks are highlighted with labeled arrows. c) Diagnostic peak intensities of mix genotype samples, varying the LDR template concentration of mutant to wild type template DNA as: 1) 0.1:1 2) 0.5:1 3) 1:1 4) 3:1 5) 5:1. d) Plot of template molar ratio against diagnostic peak intensity. I denotes intensity, M denotes moles, T denotes TAMRA, and F denotes Fluorescein.

Figure 18:
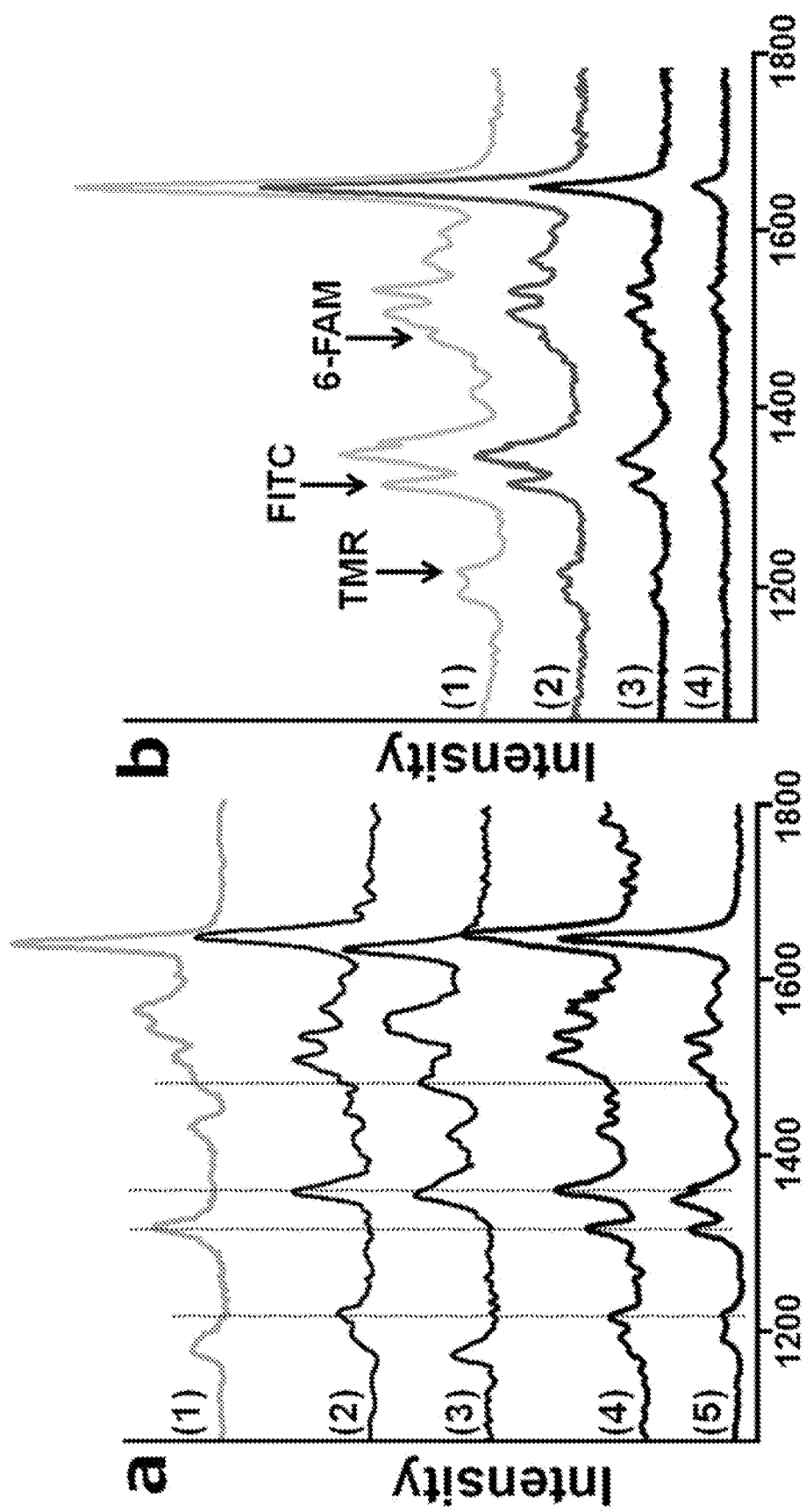

FIG. 18. Multiplex SNP samples. a) (1) G12D (Fluorescein) Mutant. (2) WT K-ras (TAMRA). (3) G12A (6-FAM) Mutant. (4) WT & G12D 2-plex (5) WT, G12D, G12A 3-plex. Dotted lines indicate diagnostic peaks. b) Dilution series of LDR three-plex containing 20 pmol template. (1) Undiluted. (2) 1:2 Dilution. (3) 1:4 Dilution. (4) 1:10 Dilution.

Figure 19:
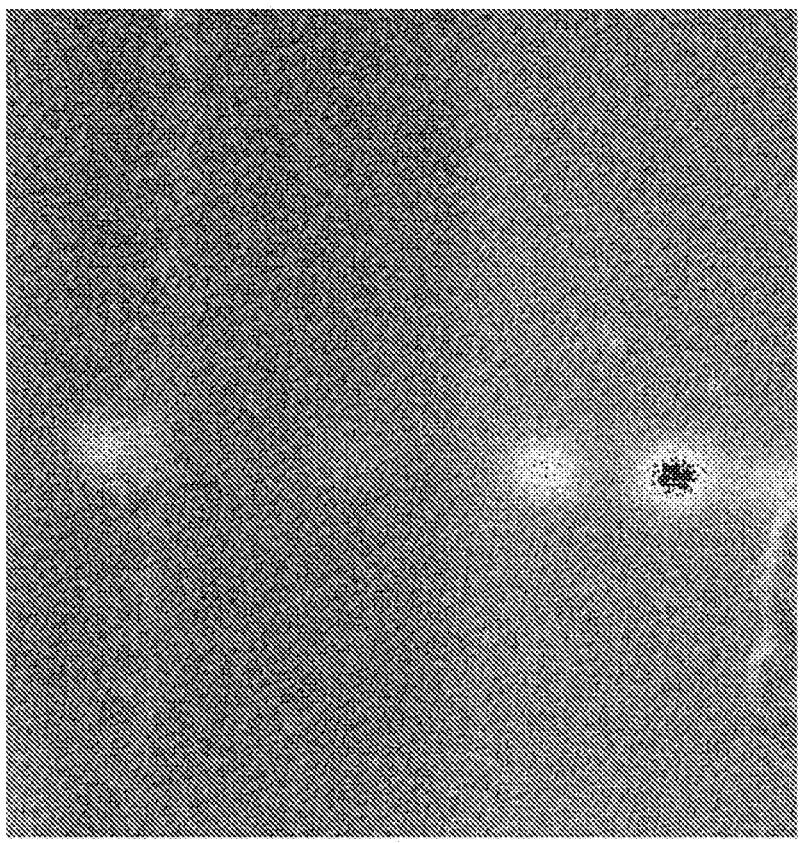

FIG. 19. 1.8% agarose gel of pre-ligation functionalized LDR reaction, Four spots visible. Top spot—fluorescent band containing nanoparticles with fluorescent primer ligated to them. Second from top spot—excess primer bound to template. Third from top spot—ligated product not on nanoparticles. Fourth from top—excess fluorescent primer.

5. DETAILED DESCRIPTION OF THE INVENTION

5.1 Microfluidic SERS Detection Device

A microfluidic detection device (or chip) is provided for detecting a nucleic acid sequence of interest (e.g., a SNP)

using SERS. Any general SERS-based detection may be used with the microfluidic detection device. In one embodiment, the microfluidic SERS detection device comprises three functional layers: a lower substrate that contains an attraction ("lower") electrode, a dielectric layer in which microchannels and microwells are positioned, and an upper electrode. The dielectric layer can be formed from any suitable polymer or other dielectric substance known in the art. In a specific embodiment, the dielectric layer comprises polyimide (PI).

In a specific embodiment, the microfluidic detection device can comprise:

a lower substrate, wherein the lower substrate comprises a lower electrode, the lower electrode being an attraction electrode;

a dielectric layer, wherein at least one microchannel and one microwell are positioned in the dielectric layer, and an upper electrode.

In another embodiment, the upper electrode is an electrically functionalized electrode.

In other embodiments, the microfluidic SERS detection device can comprise a PCR thermal cycler, a chamber for mixing ligase detection reaction (LDR) primers and amplified sample, a laser, or a SERS detector.

The microfluidic SERS detection device can also comprise one or more optical ring resonators for excitation. Ring resonators and methods for their excitation are well known in the art.

The microfluidic SERS detection device can comprise one or more structures for concentrating and/or mixing analytes, e.g., an electrokinetically active (or "electroactive") microwell (Cordovez, B. et al. 2007. *Trapping and storage of particles in electroactive microwells. Applied Physics Letters* 90, 024102, DOI:10.1063/1.2430775). The electrokinetically active microwell can be located (e.g., embedded) within the detection device (FIG. 3). In one embodiment, the microfluidic SERS detection device can comprise a chamber, wherein the electrokinetically active microwell is positioned in the chamber, wherein the lower electrode is positioned below the microwell and the upper electrode is positioned near or above the microwell and in the chamber.

In one embodiment, the electrokinetically active microwell in the microfluidic device can be used to enhance solution phase mixing of analytes. In a specific embodiment, the analytes are target nucleic acids and/or solution phase Raman enhancers.

In another embodiment, the electrokinetically active microwell can be used to increase the concentration of a sample, e.g., of analytes, for greater detection sensitivity.

Optical interrogation of the sample and/or analytes can be performed in the microfluidic SERS detection device based on electroosmotic and/or electrophoretic effects. Such interrogation can be performed using methods known in the art.

Another embodiment of the microfluidic SERS detection device is shown in FIG. 7. This embodiment comprises a lower electrode that is located on a Pyrex glass substrate, the microwell array and an upper, electrically functionalized PDMS gold electrode. One of the plurality of microchannels (labeled as "inlet port" in FIG. 7) is used to transport the sample and Raman enhancers into the mixing chamber. The upper, gold electrode patterned PDMS layer is shown in FIG. 7*b*. The optical arrangement for recording the SERS signal is shown in FIG. 7*c*. Microwells (shown in FIGS. 7*d-c*) are used to attract and concentrate SERS enhancers from the solution so they can be optically probed. Applying the polarity shown attracts particles (FIG. 7*d*) and rejects them (FIG. 7*e*).

The microwells and microchannels of the microfluidic SERS detection device can be of any dimensions suitable for microfluidic devices known in the art.

Prior art LDR approaches to SNP detection utilize fluorescent dyes attached to the LDR primers. Since there is overlap in dye frequencies, at most four target nucleotide sequences (e.g., SNPs) within a single genetic sample can be tested for at a time. The microfluidic SERS detection device disclosed herein combines the advantages of homogeneous and heterogeneous based detection systems with the capability of multiplexing and the lack of spectral overlap.

Using microfluidic SERS detection device, the number of SNPs that can be tested for at the same time is 2-30. In other embodiments, the detection device can detect at least 30 SNPs at the same time.

The microfluidic chip design can be applied to the sensitive and specific detection of any nucleic acid sequence of interest. For example, nucleic acid sequences associated with any pathogen known in the art. e.g., bacteria, viruses, etc. can be detected. Nucleic acid sequences associated with any disease (or disease state), disorder, condition or genetic characteristics can be detected. The rate and degree of physical concentration in the electrokinetically active microwell can be quantified as a function of the applied potential as described herein.

The microfluidic SERS detection device can be employed as a miniaturized biomolecular analysis system for use in fields such as pharmaceuticals testing and the detection of biological warfare agents.

5.2 Ligase Detection Reaction (LDR)-Surface Enhanced Raman Scattering (SERS) Method for Detecting Target Nucleic Acid Sequences The invention provides a method for molecular or biomolecular detection. In one embodiment, the method detects nucleic acids or nucleotide sequences of interest. Any nucleic acid or nucleotide sequence of interest (also referred to herein as "target" nucleic acid/nucleotide sequence) can be detected using the method. In as specific embodiment, the nucleic acid is a SNP.

In one embodiment, the method comprises performing a binding or hybridization reaction, performing surface enhanced Raman scattering (SERS) on the reaction, and analyzing (or quantifying) the outcome of the reaction, wherein the analyzing comprises detecting an emitted Raman signature. Any molecular or biomolecular binding or hybridization reaction known in the art is suitable for analysis using the method.

A method for detecting a binding pair of interest is also provided. The method can comprise the steps of:

performing a molecular binding reaction;

performing surface enhanced Raman scattering (SERS) on the hybridization reaction; and analyzing the outcome of the hybridization reaction, wherein the analyzing step comprises detecting an emitted Raman signature.

In one embodiment, the method detects a nucleic acid sequence of interest.

In another embodiment, the molecular binding reaction is a nucleic acid hybridization reaction.

In another embodiment, the nucleic acid hybridization reaction is a ligase detection reaction (LDR) or a ligase chain reaction (LCR) (Barany, F. *Proc. Natl. Acad. Sci. U. S. A*, 1991, 88, 189).

In another embodiment, the binding pair of interest comprises a nucleic acid sequence of interest.

In another embodiment, the nucleic acid sequence of interest is a SNP or point mutation.

In another embodiment, the method can comprise the steps of:

i) providing at least one pair of ligase detection reaction (LDR) primers:

ii) amplifying a sample of a nucleic acid sequence of interest;

iii) mixing the primers and the sample for a desired period of time;

iv) optionally concentrating the sample with or without bound primers;

v) probing the sample with a laser;

vi) detecting a surface enhanced Raman scattering (SERS) signal;

vii) analyzing the SERS signal, wherein the analyzing step comprises detecting a LDR primer signal; and viii) identifying the nucleic acid sequence of interest associated with the detected LDR primer signal.

In a specific embodiment, the method comprises performing a ligase detection reaction (LDR) (also known as "oligonucleotide ligase assay"), performing surface enhanced Raman scattering (SERS) on the LDR, and analyzing (or quantifying) the outcome of the LDR, wherein the analyzing step comprises detecting an emitted Raman signature.

FIGS. 1 and 6 illustrate overviews of one embodiment of the method, referred to herein as the "LDR-SERS" method. In the embodiment illustrated in FIG. 1, the LDR-SERS method is used for SNP detection. In the embodiment illustrated in FIG. 6, the LDS-SERS method is carried out in a microfluidic SERS detection device and is used for point mutation detection A pair of LDR primers is used for each target nucleic acid sequence of interest to be detected. A Raman enhancer (for example, a nanobead of Au or Ag) is bound to the first of the pair of LDR primers. Any Raman enhancer known in the art can be used, for example, a nanobead of Au, Ag, Cu or Na, Li, Al, Pa, In, Zn or Cd. The second of the pair of LDR primers is bound to a reporter. The reporter can be any Raman reporter known in the art, including, but not limited to dyes such as Bodipy, Yakima Yellow, Cy5, Cy3, TAMRA and FITC.

The Raman enhancer and the reporter are bound at locations on the primers that bring them into proper proximity (such that the Raman signal from the reporter can be detected) upon ligation of the LDR primers in the presence of a nucleic acid sequence of interest matching both LDR primers. The two LDR primers anneal onto a nucleic acid (e.g., DNA) at the site of a desired target nucleic acid template or sequence (e.g., a SNP). If the primers match the template perfectly, ligation of the primers occurs. Only when the primers are ligated is the Raman enhancer bound to the one primer and the reporter bound to the other primer brought into sufficiently close proximity to enable the reporter's Raman signature to be strongly emitted.

In one embodiment, the LDR-SERS method comprises: i) providing at least one pair of ligase detection reaction (LDR) primers, (ii) amplifying a sample of the nucleic acid sequence (e.g., DNA) of interest, (iii) mixing the primers and the sample for a desired period of time, (iv) optionally concentrating the sample with or without bound primers, (v) probing the sample with a laser, (vi) detecting a surface enhanced Raman scattering (SERS) signal, (vii) analyzing the SERS signal, and (viii) identifying the nucleic acid sequence of interest (e.g., SNP) associated with the LDR primer signal detected.

Methods for conducting Raman spectroscopy measurements are well known in the art. Exemplary methods for conducting Raman spectroscopy measurements are described in Section 6 (Examples).

The LDR-SERS method can be used to simultaneously detect, in certain embodiments, at least 20 or at least 30 different SNPs, so multiple pairs of LDR primers can be provided in the sample. Thus in another embodiment, the method can additionally comprise disambiguating multiple SERS signals that occur if multiple target nucleic acids of interest (e.g., SNPs) exist in the sample). Methods for disambiguating multiple signals are well known in the art.

The use of unique nanoparticle shapes and assemblies, resonance effects and multiple wavelength interrogation can be used in conjunction with the LDR-SERS method to enhance sensitivity and specificity.

A composition is also provided. The composition can comprise first nucleic acid primer, the first primer comprising a Raman enhancer bound internally in the first primer.

In one embodiment, the composition can further comprise a second nucleic, acid primer, the second primer comprising a Raman reporter bound to the second primer.

In another embodiment, the Raman reporter is bound internally.

In another embodiment, the Raman enhancer of the first primer and the Raman reporter of the second primer are bound at locations that bring them into proximity when bound to a nucleic acid sequence matching both the first and second primers, and the Raman signal from the Raman reporter can be detected upon ligation of the first and the second primers in the presence of the nucleic acid sequence matching both the first and second primers.

In another embodiment, the locations are internal locations.

In another embodiment, the first primer is LDR or LCR primer.

In another embodiment, the first and second primers are a pair of LDR or LCR primers.

In another embodiment, the binding of the Raman enhancer to the first primer is mediated by binding of the Raman enhancer to an exposed amine group on the first primer.

In another embodiment, the exposed amine group on the first primer is an amine-modified deoxythymidine with a c6 spacer.

A method for a producing a Raman enhancer primer for LDR or LCR is also provided. In one embodiment, the method comprises:

a. designing an amine-labeled primer such that a reactive amine is moved away from the ligation site;

b. introducing a hairpin into the primer;

c. reacting amine-labeled primer with NHS ester of thioctic acid in aqueous solution; and d. binding reacted product to nanoparticles prior to ligation.

5.3 Method for Concentrating and/or Mixing Analytes

A method is provided for increasing the number of reactions among a plurality of analytes in a given amount of time. The method comprises concentrating analytes and/or promoting mixing of analytes using the microfluidic SERS detection device. The method can comprise providing a microfluidic SERS detection device that comprises an electrokinetically active microwell and optionally, an optical ring resonator for excitation, placing a sample of a plurality of analytes of interest in the electrokinetically active microwell, applying alternating electrical biases across electrodes in the electrokinetically active microwell to cause the plurality of analytes to be pulled into the microwell and expelled from the microwell. The into- and out-of-the-well movement promotes mixing that enhances the reaction of the analytes (e.g., a reaction between binding partners such as binding of LDR primers to the nucleic acid template) in the solution. The ability to pull analytes into the microwell enables concentration of final product and generation of a larger SERS signal upon probing the microwell with a laser.

The method can be used for the mixing of any one or more analytes of interest in a sample. In specific embodiments, analytes are binding partners for a binding reaction, e.g., a hybridization reaction.

The electrokinetically active microwells can be used to both enhance solution phase mixing of the target nucleic acids and solution phase Raman enhancers and provide sample concentration for greater detection sensitivity. For example, optical interrogation based on electroosmotic and/or electrophoretic effects can be performed using methods known in the art.

The concentration performance of one embodiment of the detection device has been characterized using 44 nm polystyrene nanoparticles. The detection device can exhibit enhanced concentration of greater than 90% within 2.5 s when potentials between 1 and 2 volts were applied between an upper electrode and the bottom of the well. Using Dengue virus serotype 2 (DENV-2) sequences, SERS signals can be detected with a limit of detection on the order of 30 pM.

The following examples are offered by way of illustration and not by way of limitation.

6. EXAMPLES

6.1 Example 1

A Surface Enhanced Raman Scattering-Based Ligase Detection Reaction

6.1.1 Overview

Genomics provides a comprehensive view of the complete genetic makeup of an organism. Individual sequence variations, as manifested by single nucleotide polymorphisms (SNPs), can provide insight into the basis for a large number of phenotypes and diseases including cancer. The ability rapidly screen for SNPs will have a profound impact on a number of applications, most notably personalized medicine. This example demonstrates a new approach to SNP detection through the application of Surface Enhanced Raman Scattering (SERS) to the Ligase Detection Reaction (LDR). The reaction uses two LDR primers, one of which comprises a Raman enhancer and the other of which comprises a reporter. In LDR, one of the primers is designed to interrogate the SNP. When the SNP being interrogated matches the discriminating primer sequence, the primers are ligated and the enhancer and reporter are brought into close proximity enabling the reporter's Raman signature to be detected. By detecting the Raman signature of the reporter rather than its fluorescence emission, this technique avoids the problem of spectral overlap that limits the number of reactions that can be carried out in parallel by existing systems. This example demonstrates an exemplary LDR-SERS reaction for the detection of point mutations in the human K-ras oncogene. The reaction is implemented in an electrokinetically active microfluidic device that enables physical concentration of the reaction products for enhanced detection sensitivity and quantization.

The limit of detection observed was 20 pM of target DNA with the anticipated specificity engendered by the LDR platform.

6.1.2 Introduction

This example describes a method for detecting SNPs using the microfluidic SERS detection device that combines the selectivity and ease of use of the LDR reaction with the potential for large bandwidth and sensitivity of surfaced enhanced Raman spectroscopy (SERS) (Wang, D. G.; et al. *Science* 1998, 280, 1077; Fabris, L. et al. *J. Am. Chem. Soc.* 2007, 129, 6086; Doering, W. E. et al. *J. Phys. Chem.* B 2002, 106, 311). The LDR for discrimination of alleles is more accurate than the common hybridization reaction, provides high sensitivity and parallel analysis of several loci directly on genomic DNA in order to distinguish point mutations (Barany, F. *Proc. Natl. Acad. Sci. U.S.A.* 1991, 88, 189).

One embodiment of the method is illustrated in FIG. 1. The upstream primer is bound to a SERS active reporter and the discriminating 3' base, while the downstream primer is bound to an amine to which a silver nanoparticle (which acts as the SERS enhancer) is attached. When the two upstream and downstream primers are ligated together which occurs in the case of a perfect match with the template DNA), the reporter is brought into close proximity to the nanoparticle and its Raman signature is detectable. In the case where ligation is not successful, the reporter and nanoparticle remain separated and SERS enhancement will not occur. This example demonstrates the LDR-SERS detection reaction and its application to the detection of point mutations in the K-ras oncogene. The reaction is implemented in a microfluidic SERS detection device comprising electrokinetically active microwells that enables enhanced SERS detection by concentrating the reaction products from hulk phase into a confined volume for enhanced optical interrogation. In addition to SNP detection, the quantitative nature of the reaction is demonstrated and the limit of detection is characterized.

6.1.3 Experimental Section

Materials

All chemicals and solvents were purchased at the highest purity grade available. For the SERS enhancers, 50 nm diameter silver colloid solutions were purchased from Nanocs (New York, N.Y.). The buffer solution used was 10 mM phosphate-buffered saline (PBS) buffer solution (0.6 M NaCl, pH 7.6) and stored in a freezer until use. Poly(dimethylsiloxane) (PDMS) microfluidics were made using a Sylgard® 184 silicon elastomer kit (Dow Corning, Midland, Mich.). The thermostable ligase 9°N™ DNA Ligase was purchased from New England Biolabs Inc. that included a buffer for the LDR reaction. All reactions were carried out at room temperature unless otherwise specified.

LDR Reaction

The oligonucleotide sequences of all the probes and templates used in these experiments are shown in Table 1. All DNA primers and templates were synthesized by integrated DNA Technologies (Coralville, Iowa) and adapted using methods modified after Khanna et al. (Wabuyele, M. B. et al. *Anal. Chem.* 2005, 77, 7810). During primer design, the fluorophore and the amine by which nanoparticles are attached were placed 14 bp apart. To maximize the Raman signal, the enhancer and fluorophore must be as close together as possible. The LDR reaction contained the following in 10 μl reaction: 25 pM of template, 100 pM of each primer, 1 μl of ligase, 1 μl of 10× Buffer, and water to 10 μl, The LDR reactions used the following thermocycler program were as follows: 1) at 90° C. for 2 min 2) at 90° C. for 30 sec 3) at 50° C. for 4 min 4) Repeat Steps 2-4 100 times.

LDR Functionalization and Purification

The LDR reaction mixture was treated with 2 µl of DMSO to lower the melting temperature of the single stranded template and primers and reduce post-ligation binding to each other. 100 picomoles of the NHS ester of thioctic acid was added to the treated LDR reaction and allowed to react for one hour. Thioctic acid was chosen as a linker due to its high affinity for Ag and greater stability than thiols when coupling oligonucleotides to nanoparticles (Dougan, J. A. et al. *Nucl. Acids Res.* 2007, 35, 3668). The amine modification present in the primer is an amine modified deoxythymidine with a c6 spacer. The reaction mixture was then added to 200 µl of 50 nm Ag nanoparticles and allowed to react for 1 hr. After the reaction, the solution was put onto a 37 mL size exclusion column using Superdex 200 resin and flowed at 2 mL/min using DW eluent solution. The first elution peak by Abs280 was collected and determined to be the particles. Further evidence of purification is seen by the negative control where fluorophore conjugated DNA is exposed to the silver nanoparticles then purified. Very little signal is seen as compared to the experimental samples. The particles were then concentrated using a 30 kD spin filter, spinning at 2500 g for 1.5 min intervals and resuspending completely between spins. It is important to note that if the particles are not resuspended or are spun too hard, they will irreversibly stick to the filter membrane.

Gel Shift Assay

An expected positive and negative LDR reaction were run on a 3% Low-Melt temp TAE agarose gel for 50 min at 200 V in a cold room and subsequently stained with ethidium bromide (FIG. 2, Lanes 1-5) or directly (FIG. 2, Lanes 6-7). LDR-SERS reactants and products were characterized via fluorescent imaging after ethidium bromide staining as compared to DNA fragments of known size (FIG. 2. Lanes 1-5). Gaffney et al. (Gaffney, R. et al. *J. Mol. Diagn.* 2003, 5, 127) reported that the allelic probes can be designed to have unique lengths, so that the wild type and variant ligation products can be separated and detected on the basis of size. In this study, the allelic probes were labeled with fluorophores, enabling the ligation products to be additionally discriminated by the presence of fluorescence without being stained by ethidium bromide (FIG. 2, lanes 6 and 7).

Microfluidic Device

FIG. 3 shows a schematic of one embodiment of the microfluidic SERS device. As discussed above, in addition to the sample delivery channels, the active element in the device are electrokinetically active microwells, which serve to rapidly concentrate the reaction products from the bulk solution phase into a confined volume for optical probing.

The overall structure consists of three functional layers, namely, a lower substrate that contains the attraction electrode, a polyimide (PI) dielectric layer into which the channels and microwell were defined, and an upper electrode. The device was manufactured by first spinning positive and lithographically patterning photoresist S1813 (Shipley, Marlborough, Mass.) onto a Pyrex substrate to define the lower electrode pattern. Following this, 5 nm Ti/50 nm gold was evaporated and a lift off process carried out with 1165 photoresist stripper (Shipley Microposit) overnight, leaving the lower electrode, on the glass surface. A two layer photoactive PI process was used to pattern the microchannels and wells as shown in FIG. 3. The upper gold electrode was patterned on PDMS using a similar technique to that described by Lee et al. (Lee, K. et al. *Adv. Funct. Mater.* 2005, 15, 557). To bond the upper and lower surfaces, both layers were activated in oxygen plasma and the two halves were aligned and pressed together using a custom-built aligner, which are known and available in the art.

To record the SERS emission spectrum, the LDR-SERS products were concentrated in the microwell by applying the attraction potential. The approach uses electrokinetically active microwells to physically concentrate the bulk phase reaction product into a well defined volume for optical interrogation. For each of the measurements reported here, spectra are taken from 3 different points in the 10 µm well (using a 2 µm laser spot size) and report the average measurement (with error bars to indicate the standard deviation).

The excitation laser was focused at the microwell through the upper gold electrode patterned PDMS layer. In all cases a Hewlett-Packard 6234A dual output power supply and a Keithley 236 were used to apply and measure the electrical potentials.

Raman Spectroscopy Measurements

Raman spectroscopy measurements were made using an inVia Raman microscope spectrometer coupled to a Leica microscope. The experiments were conducted by focusing the excitation laser on the electro-active microwell. The 488 nm line of an $Ar^+$ ion laser was used as optical excitation source and the scattered signal was collected by a Peltier-cooled CCD detector. A 50× (NA=0.55) objective lens was used to focus the laser beam spot onto the sample surface with diameter of about 2 µm. Wave-numbers ranging from 1100 $cm^{-1}$ to 1800 $cm^{-1}$ were examined here.

6.1.4 Results and Discussion

Description of SERS Enhanced LDR Reaction

The reporter system for LDR based SNP detection reaction described in this example is based on the use of surface enhanced Raman spectroscopy (SERS). The SERS effect is related to the phenomenon of plasmon resonance, wherein metal nanostructures exhibit a pronounced optical resonance, due to the collective excitation of conduction electrons in the metal, in response to incident electromagnetic radiation, (Tuan, V.-D. IEEE *J. Select. Topics Quantum Electron.* 2008, 14, 198). The plasmons result in a significant localized enhancement in the magnitude of the electromagnetic field surrounding the particle. (Fang, C. et al. *Biosen. Bioelectro.* 2008, 24, 216; Qian, X. et al. *Am. Chem. Soc.* 2008, 130, 14934; Hering, K. et al, *Anal. Bioanal. Chem.* 2008, 390, 113). SERS active, molecules located in the near field region of the optical nanostructures are therefore exposed to a larger electromagnetic intensity than that of the excitation light and thus enhancing the strength of its Raman scattered light. Most current SERS-based detection schemes involve the immobilization of the fluorophore labeled nucleic acids on a solid surface. (Tuan, V.-D. IEEE *J. Select Topics Quantum Electron.* 2008, 14, 1.98; Hering, K. et al. *Anal. Bioanal. Chem.* 2008, 390, 113; Jung, H. Y. et al. *Anal. Chim. Acta* 2007, 602, 236). The SERS spectra are then generated based upon the proximity of the DNA and its fluorophore to the surface. Challenges with surface tethered systems include steric hindrance (and therefore a limitation in the accessibility of the target DNA) and the longer reaction time required for heterogeneous reactions. The advantage of electrokinetically active microwell used here is that it enables active mixing to enhance the rate of binding between the SERS enhancers and the biomolecular targets as well as rapid concentration of the product for surface phase optical interrogation and enhanced sensitivity.

The use of unique nanoparticle shapes (Jackson, J. B. et al. *J. Appl. Phys. Lett.* 2003, 82, 257) and assemblies (Graham, D. et al. *Nat. Nano* 2008, 3, 548; Chaney, S. B. et al. *Appl. Phys. Lett.* 2005, 87), resonance effects (Mahajan, S. et al, Phys. Chem. Chem. Phys. 2007, 9, 6016) and multiple wavelength interogation[52] can be used in conjunction with the LDR-SERS method to enhance sensitivity and specificity.

In the LDR-SERS method, a nanoparticle Raman enhancer is incorporated directly into one of the LDR probes, which allows the reaction to proceed homogenously. FIGS. 1 and 6 illustrate overviews of embodiments of the LDR-SERS method as used for SNP or point mutation detection. For simplicity a single set of PCR products is presented with two LDR probes. In this embodiment, one LDR probe is internally modified to contain a fluorophore reporter and the other is internally modified with an exposed amine group. Following enzymatic ligation, the exposed amine group reacts with a single silver (Ag) nanoparticle as shown. If the two fragments match exactly the template sequence (FIG. 1*a*), the ligase will ligate them and the fluorophore and Raman enhancer (e.g., silver nanoparticle) will be held in close proximity. Since the Raman enhancement is dependent upon the distance between the fluorophore and the nanoparticle (NP), a strong SERS signal can be detected in the case where positive ligation occurs. In the case where a base pair mismatch exists (FIG. 1*b*) the probes are not ligated and the fluorophore's Raman spectrum cannot be detected.

LDR Based Detection of Point Mutations in the K-ras Oncogene

The efficacy of the LDR primers against their respective SNP targets was initially tested by using traditional gel electrophoresis (FIG. 2). Each LDR reaction contained the amplified template DNA, the wild type or mutant LDR primer with a fluorescein modified deoxythymidine tag, and the common LDR primer. For the upstream primer and downstream primer, a band of the predicted size (20 bp) was observed at lane 2 and lane 3. As shown in FIG. 2*b*, lane 2 was brighter than lane 3 with the same molarity because the mutant LDR primer (lane 2) contained the fluorophore. To verify the presence of the expected LDR product, two LDR reaction products reacted using the mutant template (MT, lane 4) and wild type template (WT, lane 5). For the positive sample, the band of LDR reaction size (40 bp) was observed (lane 4) because the two fragments match exactly to the template sequence, resulting in the generation of a longer oligonucleotide, compared to the starting primers. For negative control (lane 5), however, a band of the expected LDR reaction size (40 bp) was not detected since the mutant primer and WT template were mismatched at the discriminating base of the upstream primer. After the LDR reaction, in order to obtain the higher SERS detecting sensitivity, the reacted samples were purified by size exclusion column.

Electroactive Microwells for Enhanced SERS Signal Detection

One embodiment of the microfluidic SERS detection device ("chip," FIG. 3) comprises a glass substrate with lithographically patterned electrodes. The substrate and electrodes were covered with an electrically insulating dielectric layer, in this case polyimide (PI), into which microwells were etched (FIG. 3). In the embodiment shown in FIG. 3, the microwells were 10 μm in diameter.

To enable delivery of nanoparticles to the wells, microfluidic structures were then defined in the dielectric polyimide (PI) layer using standard lithography techniques. After completion of the dielectric polymer layer, the PDMS fluidics were aligned and bonded to the bottom substrate such that the wells aligned with the spaces in the upper electrodes as shown in FIGS. 3*b* and 3*c*.

By applying electric potential between the upper and lower electrodes, the solution phase targets were concentrated into the wells as they flowed over them. Once concentrated, the wells were interrogated optically through the upper PDMS as shown in FIG. 3*a*.

When the SERS active LDR products were introduced into the chip via two inlet ports into the chamber, concentration was performed by applying potential of 1.5 V. This concentration step was found to increase the reproducibility and intensity of the SERS signal to the point where the spectrum could be recorded in as little as 15 s.

On-Chip LDR-SERS Detection of Point Mutations in the K-ras Oncogene

The LDR-SERS method was used to detect low-abundant DNA point mutations in K-ras oncogenes with the allelic composition evaluated at one locus. As discussed in the introduction above, the K-ras oncogene has been associated with a variety of cancers including lung, colorectal, and pancreatic malignancies. To characterize the reaction, experiments were conducted using the K-ras mutation described in Table 1. The K-ras mutation has been shown to possess a high diagnostic value for colorectal cancers. (Hashimoto. M. et al. *Biosen. Biolelectro.* 2006, 21, 1915). In the first series of experiments, a downstream primer containing the amine was reacted with the NHS ester of thioctic acid (see FIG. 1). The resulting chemical reaction served as a linker between the silver nanoparticles and the DNA primer. The resulting downstream primer was then introduced into an LDR reaction containing the upstream primer and template. In this case the LDR reaction failed. After subsequent testing, it was found that the ligation reaction would not proceed with the nanoparticle attached to the primer so close to the ligation site. Through these initial results, it was confirmed that pre-ligation chemistry and post-reaction purification were both important to successful detection.

For the on-chip assays, the LDR products described above were introduced into the chip via their respective inlet ports into the central chamber (FIG. 3), where the concentration was performed, at as flow rate of 5 μL s$^{-1}$. After filling the chamber, the SERS active LDR products were attracted into the wells for 15 s at an applied potential of 1.5 V. To obtain the SERS signal, the excitation laser was focused at the microwell and the spectrum recorded integration time set to 15 s.

Chip regeneration can be accomplished by reversing the polarity and rejecting the contents back into the chamber where they can be washed out. Here, however, a new device was used for each of the different experiments in order to avoid the potential for cross-contamination.

FIG. 4 shows the SERS spectra collected on-chip for (1) a positive sample containing fluorescein modified deoxythymidine-labeled LDR-SERS products for the mutant template (denoted as FMdT-labeled MT), (2) a negative sample for the wild type template, (3) a control sample containing only silver particles and the DNA and (4) a background control sample containing silver particles and linker. The results in FIG. 4 show that almost no detectable Raman signal was observed from the control sample for random adsorption of the DNA to the particles or from the background control sample.

FIG. 4 (inset) shows the correct spectroscopic fingerprints corresponding to FMdT-labeled dye, suggesting positive detection. In the negative sample, the LDR-SERS diagnostic peaks Were much weaker suggesting the reaction was successful. Based on these results, the 1610 cm$^{-1}$ peak was used as diagnostic of a successful ligation reaction since it is prominent in the mutated spectrum and completely lost in the wild type spectrum the 1610 cm$^{-1}$. The remaining peak at 1460 cm$^{-1}$ in the wild type sample was likely due to fluorescence from non-specific binding of the unligated primers. The large difference in the inciting temperature of the primers as compared to the ligated LDR product meant that even at room temperature a significant difference was observed in the SERS spectra of the two samples.

To examine the detection threshold of the LDR-SERS method and to verify the ability for quantitative analysis, a series of experiments was conducted at different template concentrations. FIG. 5 shows the SERS spectra of FMdT-labeled MT in a microwell for various concentrations of reaction products of (1) 100 pM (2) 50 pM (3) 40 pM (4) 20 pM and (5) 10 pM. As expected, the intensity of the Raman peak decreases concomitantly with decreasing the concentration of LDR-SERS products (FIG. 5a). Consistent with the technique used by Lee et al., (Dougan, J. A. et al. *Nucl. Acids Res.* 2007, 35, 3668: Lee, D. et al. *Appl. Spectro.* 2006, 60, 373) the concentration response was quantified by observing the change in the area of the SERS peak at 1610 cm$^{-1}$. The results are plotted in FIG. 5b and fitted to a linear curve (correlation coefficient: 0.993). Below 20 pM the main diagnostic peak could not be detected. Thus the 10 pM result was omitted from the corresponding calibration curve. Based on this result, the LDR-SERS method has a limit of detection of 20 pM.

Conclusions

This example describes the development of one embodiment of the LDR-SERS method and microfluidic SERS detection device for the detection SNPs associated with mutations in the K-ras oncogene. Using SERS active LDR products related to the K-ras cancer mutation, SERS signals were detected with a limit of detection on the order of 20 pM. The example demonstrates the ability to quantify the solution concentration based on the intensity of the SERS emission. By relying on detection of the spectrally unique Raman fingerprint, rather than florescence emission this technique can be used to increase the multiplexibility of current homogenous detection schemes by avoiding the problem of spectral overlap.

6.2 Example 2

Enhanced On-Chip SERS Based Biomolecular Detection Using Electrokinetically Active Microwells 6.2.1 Introduction This example demonstrates an embodiment of the LDR-SERS method using a microfluidic SERS detection device ("chip") with electrokinetically active microwells.

The embodiment of the microfluidic SERS detection device comprises a plurality of microfluidic channels containing embedded microwells that, when electrically actuated, either locally attract or repulse species from solution through a combination of electrokinetic effects. This approach combines the advantages of existing homogeneous (solution phase) and heterogeneous (surface phase) on-chip techniques by enabling active mixing to enhance the at of binding, between the SERS enhancers and the biomolecular targets as well as rapid concentration of the product for surface phase optical interrogation.

This example describes the chip design and fabrication procedure, experimental results illustrating the optimal conditions for the concentration and mixing processes, and a numerical analysis of the flow pattern. To demonstrate the usefulness of the device, the device was applied to the quantitative detection of nucleic acid sequences associated with Dengue virus serotype 2. A limit of detection for Dengue sequences of 30 pM was observed and the technique shows excellent specificity against other serotypes.

6.2.2 Background

Surface-enhanced Raman spectroscopy (SERS) is a powerful vibrational spectroscopy technique. The phenomenon occurs when a target molecule is brought into close proximity with a metallic surface containing nanoscopically defined features or in solution next to a metallic nanoparticle with a diameter much smaller than the wavelength of the excitation

TABLE 1

Synthetic DNA template and primers used in LDR-SERS experiments

| Template/Primer | Sequence for LDR (5'-3') |
|---|---|
| WT K-ras Template | TCC ACA AAA TGA TTC TGA ATT AGC TGT ATC GTC AAG GCA CTC TTG CCT ACG CCA CCA GCT CCA ACT ACC ACA AGT TTA TAT TCA GTC ATC [SEQ ID NO: 1] |
| MT K-ras Template | TCC ACA AAA TGA TTC TGA ATT AGC TGT ATC GTC AAG GCA CTC TTG CCT ACG CCA TCA GCT CCA ACT ACC ACA AGT TTA TAT TCA GTC ATC [SEQ ID NO: 2] |
| Common LDR Primer | 5Phos$^1$/TGG CG/AmT$^2$/AGG CAA GAG TGC CTT GAC [SEQ ID NO: 3] |
| Mutant LDR Primer | GAA TAT AAA CTT GTG GTA G/Flur$^3$/T GGA GCT GA [SEQ ID NO: 4] |

$^1$5Phos denotes a 5' phosphorylation;
$^2$AmT denotes an aminated thymine;
$^3$FlurT denotes a fluorescein dT.

The underlines of the template sequence are the complementary nucleotides to both primers.
The 3' base in mutant LDR primer (bold and italic) allows for specific discrimination of the two templates.

light (D. Graham et al., *Angew. Chem.*, 2004, 76, 412). When light at the resonant wavelength is incident on the surface or particle, a plasmon mode is excited that locally enhances the electromagnetic energy in the vicinity of the target molecule, significantly enhancing the strength of the Raman scattered light. This output is molecularly specific (R. Brown et al., *Tetrahedron Lett.*, 2001, 42, 2197) and as such the spectrum obtained from SERS analysis provides much more detailed information about the molecular structure of the target molecule than those obtained using other spectroscopic techniques (such as fluorescence [Y. C. Cao et al., *Science*, 2002, 297, 1536; R. Jin et al., *Small*, 2006, 2, 375; N. A. Abu-Hatab et al., *Appl. Spectrosc.*, 2007, 61, 1116]). Though Raman scattering is traditionally used for chemical detection and analysis, (C. Meunier et al., *Journal of Non-Crystalline Solids*, 1994, 169, 37; A. Dölle et al., *J. Chem. Phys.*, 1991, 94, 3361) it can be used for biological and biomolecular applications (Y. C. Cao et al., *Science*, 2002, 297, 1536; K. Kneipp et al., *Appl. Spectrosc.*, 1998, 52, 1493; T. Park et al., *Lab Chip*, 2005, 5, 437; M. Wang et al., *Lab Chip*, 2007, 7, 630) including single molecule analysis. (H. Xu et al., *Phys. Rev. Lett.*, 1999, 83, 4357; M. Ishikawa et al., *J. Luminescence*, 2002, 98, 81). Microfluidics based SERS chips have been previously developed in the art. (T. Park et al., *Lab Chip*, 2005, 5, 437; M. Wang et al., *Lab Chip*, 2007, 7, 630; L. He et al., *Anal. Chem.*, 2000, 72, 5438; P. A. Walker et al., *Anal, Chem.*, 1998, 70, 3766; R. M. Connatser et al., *Electrophoresis*, 2008, 29, 1441-1450; L. Chen and J. Choo, *Electrophoresis*, 2008, 29, 1815-1828. In general, the advantage of microfluidic SERS analysis are reduced sample size, shorter reaction times and improved yield when compared to conventional techniques. (D. Graham et al., Angew. Chem., 2004, 76, 412; R. Brown et al., Tetrahedron Lett, 2001, 42, 2197; Y. C. Cao et al., Science, 2002, 297, 1536; R. Jin et al., Small, 2006, 2, 375; N. A. Abu-Hatab et al., Appl. Spectrosc., 2007, 61, 1116; C. Meunier et al., Journal of Non-Crystalline Solids, 1994, 169, 37; A. Dölle et al., J. Chem. Phys., 1991, 94, 3361; K. Kneipp et al., Appl. Spectrose., 1998, 52, 1493).

Two approaches can be used for carrying out a SERS detection reaction on a chip: homogeneously, where target becomes bound or absorbs onto solution phase metallic nanoparticles that act as Raman enhancers, (F. Park et al., *Lab Chip*, 2005, 5, 437; L. Chen and J. Choo, *Electrophoresis*, 2008, 29, 1815-1828) or heterogeneously, where solution phase targets interact with surface phase SERS active dusters such as roughened electrodes, (D. L. Jeanmaire and R. P. Van Duyne, *J. electroanal. Chem. Interfacial Electrochem.*, 1977, 84, 1) or precipitated silver or gold nanoparticles (NPs). (K. Kneipp et al., *J. Phys. Condens. Matter.*, 2002, 14, R597; R. Etchegoin et al., *Chem. Phys. Lett.* 2003, 375, 84). Homogeneous SERS detection reactions have the same advantages as all homogeneous reactions (i.e. faster reaction rate and relative ease of implementation) as well as enhanced uniformity and repeatability of the SERS enhancement since the nanoparticles can be synthesized with high uniformity.

Park et al. (T. Park et al., *Lab Chip*, 2005, 5, 437), for example, described the use of an alligator-teeth-shaped PDMS microchannel to promote mixing between the target analyte and the metallic colloids used as SERS enhancers. One disadvantage of the homogeneous approach however is that because the Raman enhancers are dispersed in solution, detection sensitivity are relatively low (unless enhanced microscopy techniques like confocal are used).

Heterogeneous reactions using SERS active substrates such as metal-film-over-nanospheres L. A. Dick et al. *J. Phys. Chem. B*, 2002, 106, 853) and wells (G. L. Liu and L. P. Lee, *Appl. Phys. Lett.*, 2005, 87, 074101), are also known in the art. While these systems can have fundamentally greater sensitivity (essentially concentrating the detection zone from 3D to 2D), the analysis time is typically longer (since the molecules must diffuse to the analysis site), the chip fabrication is more complicated (since nanoscopic features must be patterned) and in some cases it is difficult to obtain regular and repeatable SERS enhancement.

Optofluidic-based on-chip SERS devices have been developed to address these problems (I. M. White et al., *Optics. Express*, 2007, 15, 17433; H. Schmidt and A. R. Hawkins, *Microfluid. Nanofluid.*, 2008, 4, 3). Measor et al. (P. Measor et al., *Appl. Phys. Lett.*, 2007, 90, 211107) used liquid core optical waveguides to confine the electromagnetic energy lengthwise though a hollow microchannel, allowing it to interact with a greater number of particles. Wang et al. (M. Wang et at. *Lab Chip*, 2007, 7, 630) used a nanochannel trap to collect solution phase Raman particles at a junction between a micro- and nanochannel. In the first of these approaches, the light/particle interaction is increased but the scattered light is still dispersed and thus the signal capture efficiency may be low. The second case allows for physical concentration of the Raman enhancers but requires transport through a nanochannel potentially limiting throughput.

In this example, a microfluidic SERS detection chip is described that combines the advantages of homogeneous and heterogeneous based detection systems without the limitations of existing devices as outlined above. Briefly, the approach is based on the use of electrokinetically active microwells (B. Cordovez et al., *Appl. Phys. Lett.*, 2007, 90, 024102) that serve to both enhance mixing between the target and solution phase Raman enhancers (M. Kakuta et al., *Chem. Rec.*, 2001, 1, 395; P. B. Howell et al., *Lab Chip*, 2005, 5, 524; P. Paik et al., *Lab Chip*, 2003, 3, 253) and then physically concentrate the product for more sensitive and rapid optical interrogation. A schematic of the chip is shown in FIG. 7. This example describes the chip design and demonstrates its usefulness by applying it to the sensitive and specific detection of nucleic acid sequences associated with Dengue virus. (N. V. Zaytseva, et al., *Anal. Bioanal. Chem.*, 2004, 380, 46; A. W. E. Franz et al., *Proc. Natl. Acad. Sci. USA*, 2006, 103, 4198). Both the rate and degree of physical concentration in the wells were experimentally quantified as a function of the applied potential. A numerical analysis of the flow/transport patterns during the mixing stage was also performed. Using the Dengue probes, the quantitative nature of the detection method was demonstrated and the limit of detection of the device was characterized.

6.2.3 Materials and Methods

Chemicals

All chemicals and solvents were purchased at the highest purity grade available. For the SERS enhancers, 50 nm diameter gold colloid solutions were purchased from Nanocs (New York, N.Y.) and were diluted to a final concentration of 0.3 nM in 10 mM phosphate-buffered saline (PBS) buffer solution (0.6 M NaCl, pH 7.4).

Dengue virus serotype 2 (DENV-2) was chosen as the target analyte. There are four closely related but antigenically distinct serotypes (DENV-1-4) that pose major public health problems in over 100 countries and infect an estimated 50 million people annually. (A. W. E. Franz et al., *Proc. Natl. Acad. Sci. USA*, 2006, 103, 4198). Two oligonucleotides (denoted as DENV-2a and DENV-4a, respectively), which contain sequences from DENV-2 and DENV-4 were purchased from Operon Biotechnologies (Huntsville, Ala.). The capture probe for DENV-2a was 3' modified with as thiol-modifier containing C3 S-S functionality and had the following sequence: 5'-ATG AAG CTG TAG TCT CAC TGG AAG G C3 S-S-3 '[SEQ ID NO: 6]. The specificity of the SERS detection technique was confirmed by conducting hybridization reaction using the target DNA, DENV-2a for positive control and DENV-4a for negative control. The target probe was modified with TAMRA dye at the 5'end. The sequences of DENV-2a (positive control) and DEN V-4a (negative control) oligonucleotides are (TAMRA) 5'-TCT AGT CCTTCCAGTGAGACTACAGCTTCATCT CAC CTT G-3' [SEQ ID NO: 7] and (Cy3) 5'-CTA GTC CTTCCACCAGGAGTACAGCTTCCTCCT GGC TTC G-3' [SEQ ID NO: 8], respectively. The underlined portions of the target sequence are the complementary nucleotides to each capture probe. Stock DNA solution at a base concentration of 300 µM. were prepared using 10 mM PBS buffer and stored in a freezer until use. Poly(dimethylsiloxane) (PDMS) microfluidics were made using a Sylgard® 184 silicon elastomer kit (Dow Corning, Midland, Mich.).

Preparation of DNA Functionalized Gold Nanoparticles and Hybridization Reaction

FIG. 8 shows a schematic of a functionalized gold NPs and hybridization reaction along with an exploded view of the Raman enhancement chip used here. In this experiment 50 nm diameter gold NPs were functionalized with the capture DNA. (Y. C. Cao et al., *Science*, 2002, 297, 1536; J. F. Hainfeld and R. D. Powell, *J. Histochem. Cytochem.*, 2000, 48, 471). To immobilize the probe, 300 nM of the thiolated capture DNA was added to 0.3 nM Au colloid solution in PBS buffer solution. The reaction was allowed to proceed for 4 h at room temperature, followed by a 1 h exposure to 300 µM 6-mercapto-1-hexanol (MCH). Because MCH forms well-organized self-assembled monolayers (SAMs) on the surface, non-specifically adsorbed ssDNA is displaced, and chemically attached the thiol modified ssDNA reorients itself, making the majority of surface-bound probes accessible for hybidization.[32] A centrifugation/resuspension cycle was then repeated twice for through removal of excess reagents. The centrifugation was carried out at 10,000 rpm for 30 min. The gold NPs immobilized capture probe were resuspended to the final concentration of 3 nM capture probe in hybridization buffer and then introduced into the sample inlet port of SERS device (FIG. 7 and FIG. 8b) at the flow rate of 5 µL s$^{-1}$. Simultaneously, the TAMRA labelled target DNA in PBS buffer solution flown in through another port also at a speed of 5 µL s$^{-1}$. The two microfluidic channels merged, mixing the two streams as they were flown towards the microwell site with the attraction voltage applied (see FIGS. 7d and 1e). After a fixed collection period, additional mixing was initiated by applying an alternating current condition of 1.0 V. In all cases a Hewlett-Packard 6234A dual output power supply and a Keithley 236 were used to apply and measure these potentials. PBS buffer solution was then flown over the well at the flow rate of 5 µL s$^{-1}$ to remove non-specifically bound target. Subsequently, the electroactive microwells were probed with a 785 nm laser excitation source using a commercial Raman microscope and spectrometer (see section below on Raman spectroscopic measurements for details). For the florescent microsphere experiments, transport was recorded using Unibrain Fire-i™ software and a Sony XCD-X710 camera.

Microfabrication Procedure

FIG. 8b shows the chip assembly procedure. The device consisted of three functional layers namely a lower electrode, a polyimide (PI) dielectric, and an upper electrode. In this device, Pyrex glass was used as a bottom electrode substrate. First, the Pyrex glass was coated with positive photoresist S1813 (Shipley, Marlborough, Mass.) at 4000 rpm for 30 s. The coated glass was soft baked for 1 min at 90° C. and exposed to 75 mJ/cm$^2$ of 300 to 500 nm ultraviolet light through a mask of the desired pattern. The exposed glass was soaked in Toluene for 60 s, and post baked for 15 s at 90° C. It was then dipped in developing solution (1 part Shipley Microposit 351 concentrate to 5 parts DI water) for 28 s, rinsed in a DI water overflow chamber for 1 min, and dried with N$_2$ gas. Following this, 5 nm Ti/50 nm gold was evaporated and a lift off process carried out with 1165 photoresist stripper (Shipley Microposit) overnight, forming the lower electrode on the glass surface. As shown in FIG. 8b, the HD-8820 PI (DuPont) middle layer has a step structure that comprised a lower passivation layer and an upper microfluidic channel. The PI passivation layer was deposited on the topside of the glass substrate patterned with the lower electrode, which served to electrically isolate the electrode from the electrolyte solution when the electric field was applied. The photosensitive PI was spun on at 1400 rpm for 60 s and soft baked for 3 min at 120° C. It was patterned with 450 mJ/cm$^2$ exposure and developed using 2.38% TMAH solution (AZ 300 MIF) for 3 min. Curing was done by temperature step gradient of 130° C., 170° C., 250° C. and 320° C. for 4 h it a programmable oven. When complete, the lower PI layer had a depth of 8 µm, which represented a ~25% thickness loss in the unexposed areas due partial etching by the developer. When solutions were introduced into the chip, the only electrode locations that were exposed were the bottom of the microwell and the upper electrode surfaces. The microfluidic channel in the upper PI layer was fabricated using the same procedure.

To fabricate the upper gold electrode patterned PDMS layer a similar technique was used to that described by Lee et al. (K. J. Lee et al., *Adv. Funct. Mater.*, 2005, 15, 557). 50 nm thick gold features were first patterned on a silicon substrate. After the gold features were created, an MPTMS (3-mercaptopropyl-trimethoxysilane) film was deposited onto the top surface of the wafer using molecular vapour deposition (MVD), The MPTMS layer served as an organic adhesion layer aiding with the transfer of the gold features from the silicon wafer to the PDMS. For the bonding of the gold patterned PDMS and the glass substrate patterned by PI, the surfaces of both layers were activated in oxygen plasma. The two halves were aligned using a custom-built aligner, which are known and available in the art.

Raman Spectroscopic Measurements

Raman measurements were made using an inVia Raman microscope spectrometer coupled to a Leica microscope. The experiments were conducted by focusing the excitation laser on the electro-active microwell. The diode laser used here had an excitation wavelength of 785 nm and operated at approximately 10 mW of power. Wave-number ranges from 1100 cm$^{-1}$ to 1800 cm$^{-1}$ were examined here. A 50×long working distance objective lens was used with a spot size of 2 µm.

6.2.4 Results and Discussion

The ability to handle and concentrate nanoparticles on-chip is important for a number of biomolecular detection applications. As mentioned above, the electrokinetic SERS device developed here allows for both efficient mixing to enhance the reaction rate and concentration to enhance detection sensitivity through the use of electroactive microwells.

To quantify the concentration capability of this device, 44 nm carboxylate functionalized fluorescent polystyrene (PS) beads in 10 mM PBS buffer were introduced into the chip through the net port (FIG. 7). The PS beads had a negative ζ potential of −41 mV as reported by Nemmar et al. (A. Nemmar et al., *Am. J. Respir. Crit. Care Med.*, 2002, 166, 998). After introduction of the nanoparticles into the chamber, the electric field was applied between the upper and over gold electrodes attracting the nanoparticles into the 10 μm diameter well. The local nanoparticle concentration in the well was estimated using the gray scale intensities from the experimental images, which were analyzed for 10 s using image-analysis software (Scion Image, Scion Corp., Frederick, Md.).

FIG. 9 shows the average florescent intensity in the well as a function of time for applied attraction voltages ranging from 0.5 V to 2.0 V. The lines shown in the image represent the average of three separate measurements. As shown in FIG. 9, the rate of concentration increases with higher applied potentials. Note that for all the higher applied potentials the well reached a saturated concentration condition within 3 s. At the lower potentials (0.5 V and 0.75 V) however a steady state was reached within the same amount of time but at a lower steady state concentration. Previous results (B. Cordovez et al., *Appl. Phys. Lett.*, 2007, 90, 024102) on trapping stability in a quiescent medium showed that the trap stability can be estimated by comparing the work required to dislodge a particle from the well with the random thermal energy in the system, represented by $k_b T$, via $S=qEh/k_b T$ (where S is a non-dimensional stability parameter, q is the charge on the particle, E is the local potential field strength in the well, and h is the height of the well), Specific well occupancy was observed to be much higher under the same experimental conditions. Smaller wells get filled more since field concentration increases with decreasing well diameter, thus generating a stronger trapping force (see B. Cordovez et al., *Appl. Phys. Lett.*, 2007, 90, 024102).

In addition, the electrokinetic movement of PS particles by electrophoresis depends on differences in the migration velocity of the PS particles through the given medium under applied potential conditions. The drift velocity of a charged PS particle is expressed as the following equation: ($V_{d,i}=v_i \times F_{E,i}$, where $v_i$ and $F_{E,i}$ indicate the electrophoretic mobility of PS particles and force per PS particles by the electric field, respectively). Thus, as expected, the higher the potential that was applied between the upper PDMS electrode and the lower microwell electrode, the larger drift velocity of PS the particles had. This means that the PS particles of the highest potential are concentrated to the microwell along with faster velocity (FIG. 9a). Based on these measurements a potential strength of 1.0 V was chosen as a suitable condition for the Raman measurements, and thus will be applied for the rest of the study. To assess this device, the mixing process for hybridization reaction and the washing step was estimated using 44 nm PS particles in 10 mM PBS buffer solution. FIG. 10 shows the time-dependent images of trapping and rejection in a 10 μm well by applying the potential condition of 1 V. Similar to the results described above, 44 nm PS particles were drawn from the bulk solution into the microwell when applied using a positive voltage on the bottom electrode (FIG. 10a-c). Immediately following the concentration of PS particles, the applied potential field is switched to be ejected by reversing the polarity (FIGS. 10d and e). The switching speed was approximately 2 s consistent with the time required to obtain >66% concentration of the particles in the wells. As can be seen, the microwells allow for active repulsion of the trapped target particles by reversing the polarity of the applied potential.

To examine the electrokinetic transport processes involved in the mixing stage washing and hybridization, a three-dimensional finite element model (FEM) of the system was constructed using the COMSOL finite element package. The computational domain used here matched exactly that shown in FIG. 8b, which contains the microwell and a chamber domain. Details of the modelling procedures and general assumptions are available in earlier works (D. Erickson and D. Li, Microscale flow and transport simulation for electrokinetic and lab-on-chip applications, in *Biomems and biomedical nanotechnology*, 2006, vol. 4 (Biomolecular Sensing, Processing and Analysis, R. Bashir and S. Wereley Eds.), Kluwer Academic Publishing). Briefly however, the system is modelled with incompressible Stokes flow equations ($\eta \nabla^2 v - \nabla p = 0$, where v is the flow field, $\eta$ is the viscosity and p is the pressure), continuity equations ($\nabla \cdot v = 0$), and use a simple Laplacian to model the applied electric field ($\nabla^2 \phi = 0$, $\phi$ is the applied potential). The Stokes flow and continuity equations were subject to electroosmotic slip, $v_{eo}$, conditions at the wall of microwell and the two side walls of the chamber. The slip velocity was calculated using the Helmholtz-Smoluchowski equation $v_{eo} = -\in \zeta E/\eta$, where $\in$ is the permittivity of the medium, $\zeta$ is the surface zeta potential set here as −40 mV, (Bouriat et al. A Convenient Apparatus to Determine the Zeta Potential of Grains by Electro-Osmosis, *Journal of Colloid Interface Science*, 1999, 209, 445) and E is the field strength ($E = -\nabla \phi$). The normal flow condition ($v \cdot n = 0$) was given for the remaining two slide walls of the chamber since no pressure was applied during the mixing processes.

FIG. 11 illustrates the electrical potential distribution and net electrokinetic particle transport Streamlines computed from the summation of the electroosmotic and electrophoretic velocity using $V_{ep} = \mu_{ep} E$, where $\mu_{ep}$ is the electrophoretic mobility. For the polystyrene fluorescent microspheres used here, the electrophoretic mobility was computed using $\mu_{ep} = \in \zeta/\eta$ with $\zeta = -41$ mV. (A. Nemmar et al., *Am. J. Respir. Crit. Care Med.*, 2002, 166, 998; B. J. Kirby and E. F. Hasselbrink Jr., Zeta potential of microfluidic substrates: 2. Data for polymers. *Electrophoresis*, 2004, 25, 203). From FIG. 11a, it can be clearly seen that the applied potential (top electrode: ground, bottom electrode; 1.0 V) induces a strong trapping potential, dragging the particles from the chamber into the microwell; however when reversing the potential polarity, the concentrated particles were ejected as illustrated in FIG. 11b. These numerical trapping/repulsion analysis results are consistent with the experimental observations represented in FIG. 10.

On-Chip Surface Enhanced Raman Scattering Based Detection of Dengue Virus Sequences Using the working principle described above, a microfluidic SERS detection device was used for rapid, quantitative SERS based nucleic acid detection. The device exploited the mixing mechanism to increase the reaction rate (and thereby reduce the analysis time) and the electrokinetic concentration technique to increase the limit of detection. Gold colloidal particles are used as SERS enhancing agents here because of their long-term stability, easily controllable size distribution, and high homogeneity. (L. Chen and L. Choo, *Electrophoresis*, 2008, 29, 1815-1828).

As detailed in the Methods and Materials section above, the target DNA and gold NPs immobilized with capture probes were introduced into the chip via their respective inlet ports into the chamber, where mixing was performed as follows. The gold NPs were first attracted into the well for 5 s at an applied potential of IV and then the polarity reversed and the rejection potential applied for a further 5 s. The process was repeated a fixed number of cycles as will be described in detail later. After the mixing step, DNA hybridized gold NPs were washed to remove the excess nonspecific target probes by flowing, PBS buffer solution at a flow rate of 5 μL s$^{-1}$. In the final step the reaction products were concentrated in the microwell by applying the attraction potential. This final concentration step was found to increase the reproducibility and intensity of SERS signal. To obtain the SERS signal, the excitation laser was focused at the microwell and the spectrum recorded integration time set to 15 s.

To characterize the reaction/device specificity. SERS detection experiments were conducted using nanoparticles functionalized with probes specific to DENV-2 and introducing (in separate experiments) DENV-2a and DENV-4a targets. FIG. 12 shows the SERS spectra collected on-chip for (a) no target DNA (b) DENV-4a (negative, control) and DENV-2a (positive control). In the latter two cases the concentration of targets in solution was 3 nM. As can be seen in FIG. 12, the results show that almost no detectable Raman signal was observed from the control gold NPs, nor the gold NPs hybridized with DENV-4a. As expected, FIG. 12c shows the correct spectroscopic fingerprints corresponding to TAMRA-labelled DENV-2a.

As outlined above, each mixing cycle requires approximately 10 s to complete, thus determining the optimal number is important to minimizing the amount of time required to perform the detection. To find the optimum conditions here, the number of mixing cycle was varied in the range of 10, 20, 40, 60 and 80 cycles. FIG. 13a shows the Raman spectra of TAMRA-labelled DENV-2a at each of these points, in order to quantify the mixing performance, the change in the area of the SERS peak from 1620 to 1690 $cm^{-1}$ was monitored. As can be seen in FIG. 13b, as the number of mixing cycle increased, the SERS signal intensity increased suggesting more of the nucleic acid was captured by the nanoparticles. On the basis of the measured peak area the hybridization reaction was about 35% complete after 20 cycles. After 40 cycles, over 80% of reaction was completed. Above 60 mixing cycles only marginal increases in the SERS peak area were observed suggesting the reaction had gone to completion.

FIG. 14 shows the SERS spectra of TAMRA-labelled DENV-2a onto gold NPs in a microwell with the different concentrations of target probe (3 pM, 30 pM, 300 pM and 3000 pM). As shown in FIG. 14a, characteristic Raman peaks for the TMARA-labelled target DNA were observed as similar to previously reported results. (Y. C. Cao et al., *Science*, 2002, 297, 1536; R. Jin et al., *Small*, 2006, 2, 375; T. Park et al., *Lab Chip*, 2005, 5, 437). In this experiment, the Raman signal was taken after a final 10 s trapping time. As observed in FIG. 9a, the efficiency of concentration at 1.0 V is increased over time and was saturated above 3 s. Similar to the results shown in FIG. 13, the Raman peak from 1620 to 1690 $cm^{-1}$ was used for quantitative evaluation. As expected the intensity of the Raman peak increases concomitantly with increasing the concentration of target DNA (FIG. 14b). FIG. 14c shows the linear response of peak area with the increase in DNA concentration. Based on these results the limit of detection for the device was determined to be 30 pM.

6.2.5 Summary and Conclusions

This example reports the development of an "optofluidic" SERS chip for the detection nucleic acid sequences associated with Dengue virus serotype 2 (DENV-2). The example demonstrates how electrokinetically active microwells embedded within the device could be used to both enhance solution phase mixing of the target nucleic acids and the Raman enhancers and provide sample concentration for greater detection sensitivity through a combination of electroosmotic and electrophoretic effects. The concentration performance of the device was characterized using 44 nm polystyrene nanoparticles and it showed enhancement of more than 90% within 2.5 s when potentials between 1 and 2 volts were applied between an upper electrode and the bottom of the well. Using DENV-2 sequences, SERS signals were successfully detected with a limit of detection on the order of 30 pM, This new approach could provide a significant contribution to the ongoing efforts to miniaturize biomolecular analysis systems for fields such as pharmaceuticals testing and the detection of biological warfare agents.

6.3 Example 3

Multiplex SNP Genotyping Utilizing Ligase Detection Reaction Coupled SERS 6.3.1 Overview Single nucleotide polymorphisms SNPs) have become key diagnostic markers for genetic disease, cancer progression, and pharmacogenomics. To identity SNPs, the ligase detection reaction (LDR) is one of leading methods, combining single molecule detection limits and high specificity. This example demonstrates multiplex LDR-Surface Enhanced Raman Spectroscopy (SERS) SN genotyping scheme. The diagnostic peaks of Raman are more distinct than fluorescence and, in theory, a large number of markers with different SHS spectra cart be multiplexed in a single sample. The example demonstrates LDR-SERS multiplex SNP genotyping of K-ras oncogene alleles at 20 pM detection levels, optimization of DNA labeling as well as Raman conditions, and the linear correlation of diagnostic peak intensity to SNP concentration in mixed genotype samples. Additionally, while synthetic template DNA was previously used, genomic DNA from typed cells lines was obtained and utilized for these experiments. This SNP genotyping platform was used to correlate genotype ratios directly diagnostic Raman peak signal intensity.

6.3.2 Introduction

SNPs are clinically useful for disease diagnosis and the selection of the appropriate therapies (Nam, R. K. et al. *Clin Cancer Res* 2009: Mehta. A. M. et al. *Genes Chromosomes Cancer* 2009; Ching, A. et al. *BMC Genet* 2002, 3, 19). The ability to genotype multiple SNPs in limited clinical samples is important due to their potential for heterogeneous distribution. For example, oncogenic K-ras alleles have been detected at (G12V, G12A, G13D, and Q61R (Khanna. M. et al. *Oncogene* 1999, 18, 27-38). A K-ras genotype from a patient's tumor is highly informative, as tumors with different genotypes respond differently to treatment regiments. (Colomer, R. et al. *Clin Cancer Res* 2008, 14, 811-816; Fasching, P. et al *J Cancer Res Clin Oncol* 2008, 134, 1079-1086; Gusella, M.; Padrini, R. *Pharmacogenomics* 2007, 8, 985-996). Many methodologies have previously been developed for SNP genotyping. Strategies include primer elongation via PCR, enzymatic cleavage, hybridization, and LDR (oligonucleotide ligation), with most of them relying on a fluorescent spectra or mass spectrometry for signal output. (Kim, S.; Misra, A. *Annu Rev Biomed Eng* 2007, 9, 289-320). Fluorescence is limited as a multiplex reporter due to spectral overlap. Mass spectroscopy is able to deconvolute more complex mixtures since different mass tags can be used (Tost, J.; Gut, I. G. *Clin Biochem* 2005, 38, 335-350; Fang, K. et al. *Proc Natl Acad Sci USA* 1999, 96, 10016-10020), but the equipment is cumbersome and difficult to integrate into a diagnostic device with a small footprint The technology described in this example utilizes SERS to circumvent the spectral overlap of fluorescence spectroscopy while retaining sensitivity and accuracy of LDR for SNP detection. Detection schemes utilizing SERS are advantageous over fluorescence as Raman peaks are approximately 1 nm (McCreery, R. L. *Raman spectroscopy for chemical analysis*; John Wiley & Sons: New York, 2000) full width half maximum (fwhm) white fluorescent labels can be 100 times larger fwhm. (Lakowicz. J. R., Third Edition. ed.; *Springer Science+Business Media, LLC*: [S.I.], 2006). In addition to the LDR-SERS platform, Raman spectroscopy has been utilized for DNA identification and SNP detection using hybridization platforms (Cao, Y. C. et al. *Science* 2(102, 297, 1536-1540; Mahajan, S. et al. *J Am Chem Soc* 2008, 130, 15589-15601) as well as PCR based systems, (Graham, D. et al. *Anal Chem* 2002, 74, 1069-1074). Multiplex identification systems have been developed utilizing SERS technologies that require no additional data processing other than simple peak recognition. (Graham, D. et al. *Anal Chem* 2002, 74, 1069-1074; Jun, B. H. et al. *J Comb Chem* 2007, 9, 237-244; Sun. L. et al. *Anal Chem* 2008, 80, 3342-3349). Also, it is possible to use the entire SERS spectra to multiplex samples even when diagnostic peaks overlap. This is possible through spectral fitting analysis, which identifies peaks not discovered by linear analysis and direct observations. (Lutz. B. R. et al. *ACS Nano* 2008, 2, 2306-2314). Finally, SERS based DNA identification schemes are advantageous in that the labels do not have to be fluorescent, (Fruk. L. et al. *Chemical Communications* 2002, 2100-2101; Sun, L.; Yu, C.; Trudayaraj, *J. Anal Chem* 2007, 79, 3981-3988) lowering total probe costs. This example demonstrates the multiplex genotyping, capacity of the LDR-SERS technology and how it may be used to identify multiple SNP alleles as well as correlate signal output to allelic ratios.

6.3.3 Methods

Ligase Detection Reaction

Template DNA used in LDR reactions was genomic DNA extracted from non-diseased colon cells and DLD1 cancer cells known to harbor the G12D mutation, which were used for the WT and G12D assays respectively. The oligonucleotide sequences of all the probes and templates used in these experiments are shown in Table 2. All DNA primers were synthesized (Integrated DNA Technologies Coralville, Iowa) and adapted by previous work done by Khanna et al. (Khanna, M. et al. *Oncogene* 1999, 18, 27-38) 9° North DNA ligase and buffer were purchased from New England Biolabs. The LDR reaction contained the following in a 10 µl reaction: 20 pmol of template, 100 pmol of each primer, 1 µl of 9° N DNA ligase. 1 µl of supplied 9° N DNA ligase 10× Buffer, and water to 10 µl. The LDR reactions used the following thermocycler program in a MJ Research PTC-200 Peltier Thermo Cycler: 1) at 90° C. for 2 min 2) at 90° C. for 30 sec 3) at 50° C. for 4 min 4) Repeat Steps 2-3 29 times.

LDR Functionalization and Purification

The completed LDR reaction mixture was treated with 2 µl of DMSO, mixed, and allowed to sit for 2 mins. A total of 100 picomoles of the NHS ester of thioctic acid was added to the treated LDR reaction and allowed to react for one hr. The reaction mixture was then added to 200 µl of 60 nm Ag or Au nanoparticles and allowed to react for 1 hr and purified as described hereinabove.

Raman Spectroscopy Measurements

Raman measurements were made using an inVia Raman spectrometer (INVIA Medical Imaging Solutions, Ann Arbor, Mich.) coupled to a Leica microscope. The experiments were conducted by focusing the excitation laser on the electro-active microwell as described hereinabove. The 488 nm and 785 nm laser lines were used as optical excitation sources and the scattered signal was collected by a Peltier-cooled CCD detector. A 50× (NA=0.55) objective lens was used to focus the laser beam spot onto the sample surface with diameter of about 2 µm. Wave-numbers ranging from 1100 $cm^{-1}$ to 1800 $cm^{-1}$ were examined for all SERS experiments.

6.3.4 Results

One embodiment of the multiplex LDR-SERS scheme is shown in FIG. 15. A common primer binds 3' of the SNP, which contains an amine for post-ligation Raman enhancer coupling. A Raman active fluorophore-primer conjugate, with a discriminating base at the 3' end, binds 5' of the SNP. Ligation, and thus a Raman coupled signal, occurs only if the primer matches perfectly.

In this example, different Raman active fluorophores were placed on the SNP allele specific primers, which produced a signature Raman profile as diagrammed in FIG. 15b. As described in Table 2, a TAMRA fluorescent label was attached to the wild type discriminating primer while a fluorescein label was attached to the G12D discriminating primer. Samples containing both templates produced an aggregate spectrum that had elements of both Raman reporters, but diagnostic peaks of each marker could still be discerned and quantified. After the ligation occurs the Raman enhancer was attached to the DNA strand, purified, and then concentrated in an electroactive nanowell.

Upon examining the differences in spectra, several possible diagnostic peaks were identified with the most prominent at approximately 1315 $cm^{-1}$ and 1370 $cm^{-1}$ for fluorescein and TAMRA-labeled DNA respectively. To optimize the SERS output signal and resolution between diagnostic peaks, the interplay between laser excitation wavelength and nanoparticle enhancers was investigated.

FIG. 16a shows TAMRA labeled DNA SERS spectra as function of laser excitation wavelength and Raman enhancers. While the 785 nm excitation source (FIG. 16a3 & FIG. 16a4) provided three-fold more intense peaks at the 1500 $cm^{-1}$ cluster in the TAMRA sample, the 488 nm excitation source gave much more distinct peaks, reducing the peak width of the 1370 $cm^{-1}$ diagnostic peak by a factor of three in both the silver and gold enhanced samples. A similar pattern was seen for fluorescein-labeled DNA. The 488 nm laser provided an approximately three-fold higher signal as compared to the 785 nm excitation source for the peak at 1650 $cm^{-1}$ and a 1.4 fold average enhancement when comparing the silver enhanced samples. This is most likely attributable to a resonance Raman effect, where both dyes are excitable to their first electronic state at 488 nm but not at 785 nm (Graham, D. et al. *Anal Chem* 2002, 74, 1069-1074; Faulds, K. et al. *Angew Chem Int Ed Engl* 2007, 46, 1829-1831). Resonance Raman effects can greatly increase Raman signal, which has been previously shown in assays detecting DNA base changes using hybridization format (Cao, Y. C. et al. *Science* 2002, 297, 1536-1540).

The difference between gold and silver nanoparticle SERS enhancers was also investigated, with silver nanoparticles providing a much better signal to noise ratio as seen in FIG. 16. In the TAMRA labeled sample, silver provided an average 1.5 SNR enhancement over gold when averaging all the peaks and a 1.7-fold better SNR at the 1370 $cm^{-1}$ diagnostic peak when excited at 488 nm. An average 1.33 SNR enhancement of silver compared to gold was achieved in the TAMRA sample excited at 785 nm. In the fluorescein labeled sample, an average 3.2 SNR was achieved over gold when excited at 488 nm. SNR of the fluorescein labeled samples excited at 785 nm was not readily comparable in silver versus gold enhancements due to the large peak broadness of the gold enhanced samples. The observed, metal dependent, Raman enhancement trends conform to previously observed behavior that silver is a better Raman enhancer than gold (Zeman, E. J. et al. *J. Physical Chem* 1987, 91, 634-643).

FIG. 17 shows multiplex data obtained for a mixture of WT and G12D targets using both sets of LDR primers. FIG. 17a shows the SERS spectra profiles of a mixture of WT and G12D with silver or gold as the SERS enhancer (silver for 1 and 3, gold for 2 and 4) and excitation wavelength of 488 nm (1 and 2) and 785 nm (3 and 4). The multiplex sample conformed to the trends observed in FIG. 16, with silver nanoparticles demonstrating 1.5 and 2-fold SNR enhancement fir the fluorescein and TAMRA diagnostic peaks respectively when excited at 488 nm as compared to gold. The 488 nm laser reduced the peak width of the fluorescein and TAMRA diagnostic peaks by a factor of 1.8 and 1.2 respectively as compared to the 785 nm excitation source for silver enhanced samples.

FIG. 17b shows a resultant multiplex spectra with the fluorescein and TAMRA spectra overlaid, demonstrating that the diagnostic fluorescein peak at ~1315 cm$^{-1}$ was clearly distinguishable from the diagnostic TAMRA peak at ~1370 cm$^{-1}$, which identified the G12D mutant and wild type genotypes respectively. These spectra were obtained from silver enhanced samples excited at 488 nm.

FIG. 17c depicts the correlation of SNP concentration to signal intensity. In the mixed sample, the population of mutant (fluorescein) to wild type (TAMRA) DNA template was varied in the LDR reaction of at ratios of 0.1:1, 0.5:1, 1:1, 3:1, and 5:1 in samples 1-5 respectively. As expected, as the ratio of mutant to WT SNPs was increased, the 1315 cm$^{-1}$ signal increases while the 1370 cm$^{-1}$ signal decreases.

FIG. 17d plots the molar ratio of WT to mutant template concentration against signal intensity of the diagnostic peaks as obtained from FIG. 17c. A linear trend was generated with diagnostic signal intensity directly correlating to the genotype molar ratio. Unlike PCR, LDR did not produce exponential amplification of the product since the product of the ligation was not a template for the LDR primers. The signal was approximately linear with the initial target concentration.

FIG. 18 demonstrates three-plex capabilities of the system. In the presence of a diagnostic primers, LDR reactions were run with one, two, or three templates then functionalized with silver nanoparticles and their Raman spectra analyzed.

FIG. 18a(1) shows a diagnostic peak for the G12D mutant (fluorescein) at approximately 1315 cm$^{-1}$.

FIGS. 18a(2) and 18a(3) are representative spectra for WT (TAMRA) and G12A (6-FAM) haplotypes respectively. While 1370 cm$^{-1}$ was previously cited above as a diagnostic peak for WT templates, this peak was very close to a peak seen in the G12A spectra. An alternative diagnostic peak for the WT spectrum was seen at ~1225 cm$^{-1}$ however and could be used for WT haplotype identification. The G12A haplotype had a unique diagnostic peak at ~1488 cm$^{-1}$.

FIG. 18a(4) demonstrates that having three primers sets in the mix does not inhibit two-plex detection, as diagnostic peaks tier WT and G12D mutations were present.

FIG. 18a(5) demonstrates detection of all three haplotypes with diagnostic peaks for all three alleles clearly present.

FIG. 18b shows a dilution series to analyze limit of detection.

6.3.5 Discussion

This example presents a multiplex SNP genotyping system that utilizes a ligase detection reaction coupled SITS. The system allows accurate discrimination of multiple alleles and does not require a microarray format or capillary electrophoresis (Tobler, A. R. et al. *J Biomol Tech* 2005, 16, 398-406). In addition, the system can be used to quantify SNP allelic ratios based on relative signal intensity. The technology retains the advantages previously shown with LDR and increases the potential for multiplex detection in a simple technology platform.

Fluorophores can be used as Raman tags due to their wide availability on oligonucleotides. SERS multiplex detection of oligonucleotides labeled with common fluorophore tags has been previously demonstrated (Faulds, K et al. *Analyst* 2008, 133, 1505-1512; Lutz, B. R. et al. *ACS Nano* 2008, 2, 2306-2314). In the present system, any chromophore or molecule known in the art with a high Raman cross section and unique spectral signature can be used as a label. This opens up a very large spectral space for detection and multiplexing possibilities. The technology presented in this example can be used in point-of-care genotype analysis systems for clinically relevant SNPs. To achieve this point-of-care goal, attachment of Raman enhancers to oligonucleotides prior to the ligase detection reaction can be used.

TABLE 2

Primers used in LDR-SERS experiments

| Template/Primer | Sequence for LDR (5'-3') |
|---|---|
| Common LDR Primer | 5Phos[1]/TGG CG/AmT[2]/AGG CAA GAG TGC CTT GAC [SEQ ID NO: 3] |
| Mutant LDR Primer | GAA TAT AAA CTT GTG GTA G/FlurT[3]/T GGA GCT G*A* [SEQ ID NO: 4] |
| Wild type LDR Primer | GAA TAT AAA CTT GTG GTA G/TAM[4]/T GGA GCT G*G* [SEQ ID NO: 5] |

[1]5Phos denotes a 5' phosphorylation;
[2]AmT denotes an aminated thymine;
[3]FlurT denotes a fluorescein dT.
[4]TAM denotes a TAMRA dT.
The 3' base in mutant and wild type LDR primers (bold and italic) allow for specific discrimination of the two templates.

6.4 Example 4

Method for Pre-Ligation Functionalization of Nanoparticles and Primer Design

This example demonstrates a method for pre-ligation functionalization of nanoparticles for use in a nucleic acid hybridization reaction, e.g., a LDR. This example also describes a method for designing of a Raman enhancer primer. In this example, the Raman reporter primer was not altered.

The Raman enhancer primer was redesigned such that the reactive amine was moved to the end of the primer, away from the ligation site. A hairpin was introduced to the primer adjacent to the amine. In certain embodiments, however, it can be moved throughout the primer. Primer length and composition can vary to accommodate any sequence.

The hairpin preferably melts at ligation/annealing temperatures (45-90° C.) and re-anneals to itself at the temperature at which Raman spectra are taken (presumably ambient temperature).

To functionalize the nanoparticles, the amine labeled primer was reacted with the NHS ester of thioctic acid in aqueous solution for 2 hours at room temperature. The primer was preferably in 1.5-20 molar excess.

This reacted product was then allowed to bind nanoparticles for 18 hours. The art-known formula for determining the amount of oligonucleotide needed to coat the particles is 52.5 $SA_P C_P V_P$ Where:
$SA_P$-Surface area of particle
$C_P$-Concentration of the particle
$V_p$-Volume of the particle After the 18 hours, NaCl was added to brine the final concentration to 0.3 M. Sodium phosphate buffer pH 7.0 was also added to a final concentration of 100 mM. These additions were done in a stepwise manner from 2-50 additions over 1-10 days. After functionalization was complete, the particles were washed with the sodium phosphate butler (pH 7.0) by centrifugation to remove excess primer.

Functionalized particles were added to an LDR reaction, which reaction is described in the Examples set forth hereinabove. The functionalized particles were added to the LDR reaction as 1-50% of the solution's volume. An equimolar amount of reporter primer was added to the reaction along with the other components described in the above Examples and the reaction was run and subsequently analyzed as described above.

FIG. 19 shows a 1.8% agarose gel of a pre-ligation functionalized LDR reaction, demonstrating that ligation can be successfully performed using the Raman enhancer primer that has been functionalized with nanoparticles pre-ligation. Four spots are visible. The top spot is it fluorescent band containing nanoparticles (Raman enhancers) with the fluorescent (reporter) primer ligated to them. The second from the top spot is excess primer bound to template. The third from the top spot is ligated product not on nanoparticles. The fourth from top is excess fluorescent primer.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for detecting a nucleic acid sequence of interest in a sample comprising the steps of:
   i) providing a first LDR primer, a Raman enhancer, a second LDR primer, and a Raman reporter, wherein the Raman enhancer is bound to the first LDR primer and the Raman reporter is bound to the second LDR primer;
   ii) performing a nucleic acid hybridization reaction on nucleic acid sequences in the sample, wherein the nucleic acid hybridization reaction is a ligase detection reaction (LDR) or a ligase chain reaction (LCR), and wherein the step of performing the nucleic acid hybridization reaction comprises the step of mixing the first LDR primer, the second LDR primer and the sample for a desired period of time;
   iii) performing surface enhanced Raman scattering (SERS) on the nucleic acid hybridization reaction, wherein the step of performing SERS comprises the step of probing the sample with a laser; and
   iv) analyzing the outcome of the nucleic acid hybridization reaction, wherein the analyzing step comprises detecting a SERS signal from a binding pair comprising the nucleic acid sequence of interest, wherein the SERS signal indicates the presence of the nucleic acid sequence of interest, thereby detecting the nucleic acid sequence of interest.

2. The method of claim 1 wherein the nucleic acid sequence of interest is a SNP or point mutation.

3. The method of claim 2 wherein the nucleic acid sequence of interest is a SNP, the method further comprising the step of:
   quantifying an SNP allelic ratio;
wherein the ratio is quantified based on relative intensity of signal output.

4. The method of claim 1 further comprising the steps of:
   analyzing the SERS signal, wherein the analyzing step comprises detecting a signal from the LDR primer; and
   identifying the nucleic acid sequence of interest associated with the detected signal from the LDR primer.

5. The method of claim 1 wherein the binding pair comprises a plurality of binding pairs and wherein step (iv) comprises detecting a plurality of SERS signals from the plurality of binding pairs.

6. The method of claim 5 further comprising the step of:
   disambiguating the plurality of SERS signals.

7. The method of claim 5 wherein the plurality of binding pairs is 2-30 binding pairs.

8. The method of claim 6 wherein:
   multiple wavelengths are interrogated; and
   a plurality of SERS signals is detected.

9. The method of claim 1 comprising, after step i), the step of amplifying nucleic acid sequences in the sample.

10. The method of claim 1 comprising, after the step of mixing the first LDR primer, the second LDR primer and the sample, the step of concentrating the sample with or without bound primers.

* * * * *

SEQUENCE LISTING

```
<160> NUMBER OF SEQ ID NOS: 8

<210> SEQ ID NO 1
<211> LENGTH: 90
<212> TYPE: DNA
<213> ORGANISM: Artificial Sequence
<220> FEATURE:
<223> OTHER INFORMATION: Engineered sequence

<400> SEQUENCE: 1
tccacaaaat gattctgaat tagctgtatc gtcaaggcac tcttgcctac gccaccagct      60
ccaactacca caagtttata ttcagtcatc                                       90

<210> SEQ ID NO 2
<211> LENGTH: 90
<212> TYPE: DNA
<213> ORGANISM: Artificial Sequence
<220> FEATURE:
<223> OTHER INFORMATION: Engineered sequence

<400> SEQUENCE: 2
tccacaaaat gattctgaat tagctgtatc gtcaaggcac tcttgcctac gccatcagct      60
ccaactacca caagtttata ttcagtcatc                                       90

<210> SEQ ID NO 3
<211> LENGTH: 24
<212> TYPE: DNA
<213> ORGANISM: Artificial Sequence
<220> FEATURE:
<223> OTHER INFORMATION: Engineered sequence
<220> FEATURE:
<221> NAME/KEY: AmT2
<222> LOCATION: (6)..(6)
<223> OTHER INFORMATION: aminated thymine
```

```
<400> SEQUENCE: 3
tggcgtaggc aagagtgcct tgac                                          24

<210> SEQ ID NO 4
<211> LENGTH: 29
<212> TYPE: DNA
<213> ORGANISM: Artificial Sequence
<220> FEATURE:
<223> OTHER INFORMATION: Engineered sequence
<220> FEATURE:
<221> NAME/KEY: 3FlurT
<222> LOCATION: (20)..(20)
<223> OTHER INFORMATION: fluorescein dT

<400> SEQUENCE: 4
gaatataaac ttgtggtagt tggagctga                                     29

<210> SEQ ID NO 5
<211> LENGTH: 31
<212> TYPE: DNA
<213> ORGANISM: Artificial Sequence
<220> FEATURE:
<223> OTHER INFORMATION: Engineered sequence

<400> SEQUENCE: 5
gaatataaac ttgtggtagt amtggagctg g                                  31

<210> SEQ ID NO 6
<211> LENGTH: 26
<212> TYPE: DNA
<213> ORGANISM: Artificial Sequence
<220> FEATURE:
<223> OTHER INFORMATION: Engineered sequence

<400> SEQUENCE: 6
atgaagctgt agtctcactg gaaggc                                        26

<210> SEQ ID NO 7
<211> LENGTH: 40
<212> TYPE: DNA
<213> ORGANISM: Artificial Sequence
<220> FEATURE:
<223> OTHER INFORMATION: Engineered sequence

<400> SEQUENCE: 7
tctagtcctt ccagtgagac tacagcttca tctcaccttg                         40

<210> SEQ ID NO 8
<211> LENGTH: 40
<212> TYPE: DNA
<213> ORGANISM: Artificial Sequence
<220> FEATURE:
<223> OTHER INFORMATION: Engineered sequence

<400> SEQUENCE: 8
ctagtccttc caccaggagt acagcttcct cctggcttcg                         40
```